(12) United States Patent
Piao et al.

(10) Patent No.: US 12,024,729 B2
(45) Date of Patent: Jul. 2, 2024

(54) POLYPEPTIDE HAVING CEPHALOSPORIN C ACYLASE ACTIVITY AND USE THEREOF

(71) Applicant: AMICOGEN, INC., Jinju-si (KR)

(72) Inventors: Zhe Piao, Jinju-si (KR); Eun Seon Wang, Jinju-si (KR); Hong Xian Li, Jinju-si (KR); Mi Kyoung Lee, Jinju-si (KR); Ah Reum Son, Jinju-si (KR); Su Jin Lim, Jinju-si (KR)

(73) Assignee: AMICOGEN, INC., Jinju-si (KR)

( * ) Notice: Subject to any disclaimer, the term of this patent is extended or adjusted under 35 U.S.C. 154(b) by 0 days.

(21) Appl. No.: 18/056,385

(22) Filed: Nov. 17, 2022

(65) Prior Publication Data
US 2023/0265409 A1    Aug. 24, 2023

(30) Foreign Application Priority Data
Dec. 24, 2021   (KR) .................. 10-2021-0187761

(51) Int. Cl.
*C12N 9/80* (2006.01)
*C12N 15/63* (2006.01)

(52) U.S. Cl.
CPC ............... *C12N 9/80* (2013.01); *C12N 15/63* (2013.01); *C12Y 305/01093* (2013.01)

(58) Field of Classification Search
CPC ..................................................... C12N 9/80
See application file for complete search history.

(56) References Cited

FOREIGN PATENT DOCUMENTS

| CN | 102925423 | 2/2013 |
|---|---|---|
| CN | 103937764 | 7/2014 |
| CN | 105543201 | 5/2016 |
| CN | 105543201 A * | 11/2018 |
| CN | 109913436 | 6/2019 |
| CN | 111172142 | 5/2020 |
| EP | 1553175 | 7/2005 |
| JP | H07-222587 | 8/1995 |
| KR | 10-2005-0017832 | 2/2005 |
| KR | 10-2005-0074313 | 7/2005 |
| KR | 10-2010-0056123 | 5/2010 |
| KR | 10-2014-0094150 | 7/2014 |
| KR | 10-1728906 | 4/2017 |
| WO | 2018-165881 | 9/2018 |

OTHER PUBLICATIONS

EPO, Search Report of EP 22211393.8 dated Apr. 12, 2023.
Samuel Karlin et al., "Applications and statistics for multiple high-scoring segments in molecular sequences", Proc. Natl. Acad. Sci. USA, vol. 90, pp. 5873-5877, Jun. 1993.
William R. Pearson, "[5] Rapid and Sensitive Sequence Comparison with FASTP and FASTA", Methods Enzymol., 183, 63, 1990.
Vijay Chintaman Sonawane, "Enzymatic Modifications of Cephalosporins by Cephalosporin Acylase and Other Enzymes", Critical Reviews in Biotechnology, 26:95-120, 2006, DOI: 10.1080/07388550600718630.
Yong-Chjun Park et al., "Isolation and Characteristics of Microorganism Producing Cephalosporin C Acylase", Kor. J. Appl. Microbiol. Biotechnol. 23: 559-564, 1995.
Marion M. Bradford, "Rapid and Sensitive Method for the Quantitation of Microgram Quantities of Protein Utilizing the Principle of Protein-Dye Binding", Anal. Biochem. 72: 248-254, 1976.
GenBank: RIJ68106.1, acylase [*Brevundimonas* sp. LPMIX5], Aug. 29, 2018.
Chiaki Yamada et al., "Improvement of the Glutaryl-7-Aminocephalosporanic Acid Acylase Activity of a Bacterial γ-Glutamyltranspeptidase", Appl Environ Microbiol.,74(11):3400-3409, doi:10.1128/AEM.02693-07.
Ye Tian et al., "Computational design of variants for cephalosporin C acylase from Pseudomonas strain N176 with improved stability and activity", Appl Microbiol Biotechnol.,101(2):621-632, Aug. 24, 2016.
Dudi Hardianto et al., "Cephalosporin C Acylase from Microbes for One-step Enzymatic Transformation of Cephalosporin C to 7-Aminocephalosporanic Acid," Journal of Pure and Applied Microbiology, vol. 10, No. 4, pp. 2495-2499, Dec. 2016, doi: https://doi.org/10.22207/jpam.10.4.03.
EPO, Search Report of EP 22211393.8 dated Jul. 24, 2023.

* cited by examiner

*Primary Examiner* — Suzanne M Noakes
(74) *Attorney, Agent, or Firm* — LEX IP MEISTER, PLLC

(57) ABSTRACT

Disclosed herein are a polypeptide having cephalosporin C(CPC) acylase activity and a use thereof. More specifically, a mutant CPC acylase comprising a point mutation introduced thereinto, thereby exhibiting improved enzymatic activity and/or stability, and a use of the mutant CPC acylase for producing 7-aminocephalosporanic acid (7-ACA), are provided.

18 Claims, 2 Drawing Sheets

Specification includes a Sequence Listing.

POLYPEPTIDE HAVING CEPHALOSPORIN C ACYLASE ACTIVITY AND USE THEREOF

CROSS-REFERENCE TO RELATED APPLICATIONS

This application claims the benefit of priority to Korean Patent Application No. 10-2021-0187761, filed on Dec. 24, 2021, the entire disclosure of which is incorporated herein by reference in its entirety.

REFERENCE TO AN ELECTRONIC SEQUENCE LISTING

The contents of the electronic sequence listing (LPP20224237US SEQ Revised.xml; Size: 49.8 K bytes; and Date of Creation: Apr. 5, 2024) is herein incorporated by reference in its entirety.

BACKGROUND OF THE INVENTION

1. Field of the Invention

The present description relates to a polypeptide having cephalosporin C(CPC) acylase activity and a use thereof and, more specifically, to a mutant CPC acylase that has a point mutation introduced thereinto and thus exhibits improved enzymatic activity and/or stability, and a use thereof for producing 7-aminocephalosporanic acid (7-ACA).

2. Description of the Related Art

Cephalosporin C (hereinafter, referred to as "CPC"), which is a family of beta-lactam antibiotics, is produced by microorganisms such as *Acremonium chrysogenum*. CPC exhibits antibiotic activity against Gram-negative bacteria by inhibiting cell wall synthesis in Gram-negative bacteria, but due to its very weak activity, finds a main application in preparing raw materials for semi-synthetic cephalosporin antibiotics (hereinafter referred to as "cephalosporins"). Among others, 7-aminocephalosporanic acid (hereinafter, referred to as "7-ACA"), obtained by removing the D-alpha-aminoadipoyl side chain from CPC, is used as a raw material for most cephalosporins accounting for more than 40% of the global antibiotic market.

Conventionally, there are chemical and enzymatic processes for preparing 7-ACA from CPC. Since the chemical processes require complex reaction conditions and high environmental treatment costs, the production of 7-ACA has recently tended to resort to environmentally friendly enzymatic processes.

A typical enzymatic process consists of the following two steps: in the first step, CPC is converted into glutaryl-7-aminocephalosporanic acid (hereinafter referred to as "GI-7-ACA") through the enzymatic reaction of D-amino acid oxidase (hereinafter referred to as "DAO"); and the second step is adapted to convert GI-7-ACA into 7-ACA through the enzymatic reaction of GI-7-ACA acylase (see the left reaction scheme in FIG. 1).

However, the two-step enzymatic process suffers from the disadvantage of being low in production yield because the hydrogen peroxide produced in the enzymatic reaction of the first step attacks the substrate (CPC), the reaction product (GI-7-ACA), and DAO.

Suggested as an alternative for solving the problem is a one-step enzymatic process of producing 7-ACA directly from CPC without conducting the first step (see the right reaction scheme in FIG. 1). To this end, there is a need for CPC acylase that catalyzes the direct production of 7-ACA from CPC. Since CPC acylase does not exist in nature, it is synthesized by modifying various types of GI-7-ACA acylase (also known as glutaryl amidase (GA)) that naturally occur. However, GI-7-ACA acylase is poor in activity for CPC.

There is therefore a need for the development of CPC acylase that has an excellent enzymatic activity for CPC.

SUMMARY OF THE INVENTION

Provided herein are a CPC acylase with improved enzymatic activity for cephalosporin C (hereinafter referred to as "CPC") and a use thereof.

An aspect provides a mutant CPC acylase, derived from a CPC acylase including an alpha-subunit and a beta-subunit, wherein the mutant CPC acylase includes a mutation by substitution of at least one (one, two, three, four, or five) selected from the group consisting of:
  (i) alanine at position 11 in the alpha-subunit of SEQ ID NO: 3 (A11α);
  (ii) glycine at position 24 in the alpha-subunit of SEQ ID NO: 3 (G24α);
  (iii) alanine at position 136 in the beta-subunit of SEQ ID NO: 4 (A136β);
  (iv) isoleucine at position 179 in the beta-subunit of SEQ ID NO: 4 (I179β); and
  (v) histidine at position 453 in the beta-subunit of SEQ ID NO: 4 (H453β)
  with an amino acid different from the corresponding original amino acid residue.

In one embodiment, the mutant CPC acylase may include a mutation by at least one (one, two, three, four, or five) substitution selected from the group consisting of:
  (i-1) substitution of A11α in the alpha-subunit of SEQ ID NO: 3 with asparagine (N) (A11αN);
  (ii-1) substitution of G24α in the alpha-subunit of SEQ ID NO: 3 with aspartic acid (D) (G24αD);
  (iii-1) substitution of A136β in the beta-subunit of SEQ ID NO: 4 with threonine (T) (A136βT);
  (iv-1) substitution of I179β in the beta-subunit of SEQ ID NO: 4 with tyrosine (Y) (I179βY); and
  (v-1) substitution of H453β in the beta-subunit of SEQ ID NO: 4 with threonine (T) (H45βT).

In another embodiment, the mutant CPC acylase may further include, in addition to the aforementioned amino acid substitution, a mutation by at least one (one, two, three, four, or five, e.g., five) selected from the following substitutions in the beta-subunit of SEQ ID NO: 4:
  (vi) substitution of isoleucine at position 45 (I45β) with an amino acid different therefrom, for example, (vi-1) I45βV;
  (vii) substitution of phenylalanine at position 58 (F58β) with an amino acid different therefrom, for example, (vii-1) F58βV;
  (viii) substitution of tyrosine at position 153 (Y153β) with an amino acid different therefrom, for example, (viii-1) Y153βT;
  (ix) substitution of phenylalanine at position 177 (F177β) with an amino acid different therefrom, for example, (ix-1) F177βL; and
  (x) substitution of valine at position 382 (V382β) with an amino acid different therefrom, for example, (x-1) V382βL.

Another aspect provides a nucleic acid sequence coding for the mutant CPC acylase described in the foregoing, a recombinant expression vector carrying the nucleic acid sequence, and a recombinant cell anchoring (comprising) the nucleic acid sequence and/or the recombinant expression vector thereat.

Another aspect provides a composition for production of 7-aminocephalosporanic acid (7-ACA) or a salt thereof, the composition including the mutant CPC acylase described above, a nucleic acid molecule coding for the mutant CPC acylase, a recombinant expression vector carrying the nucleic acid molecule, a recombinant cell comprising the nucleic acid molecule and/or the recombinant expression vector, and a culture of the recombinant cell.

Another aspect provides a use of at least one, selected from the group consisting of the mutant CPC acylase described above, a nucleic acid molecule coding for the mutant CPC acylase, a recombinant expression vector carrying the nucleic acid molecule, a recombinant cell comprising the nucleic acid molecule and/or the recombinant expression vector, and a culture of the recombinant cell, for producing 7-aminocephalosporanic acid (7-ACA) or a salt thereof.

Another aspect provides a method for producing 7-aminocephalosporanic acid (7-ACA) or a salt thereof, using at least one selected from the group consisting of the mutant CPC acylase described above, a nucleic acid molecule coding for the mutant CPC acylase, a recombinant expression vector carrying the nucleic acid molecule, a recombinant cell comprising the nucleic acid molecule and/or the recombinant expression vector, and a culture of the recombinant cell.

DETAILED DESCRIPTION

Provided herein are CPC acylase having an improved enzymatic activity for cephalosporin C (hereinafter referred to as "CPC") and a use thereof.

DEFINITION OF TERMS

As used herein, the phrase that a polynucleotide (interchangeably used with "gene" or "nucleic acid molecule") or a polypeptide (interchangeably used with "protein" or "enzyme") comprises (or includes) or a "specific nucleic acid sequence" or an "amino acid sequence" or consists or is composed (essentially) of a "specific nucleic acid sequence" or an "amino acid sequence" means that the polynucleotide or a polypeptide essentially contains the specific nucleic acid sequence or amino acid sequence therein, or is construed to include or comprise a "substantially identical sequence" resulting from the impartment of a mutation (deletion, substitution, alteration, and/or addition) to the specific nucleotide or amino acid sequence to the extent of retaining the original function and/or desired function of the polynucleotide or polypeptide.

In an embodiment, a polynucleotide or a polypeptide "includes (comprises) a specific nucleic acid sequence or an amino acid sequence" or "(essentially) consists of or represented by a specific nucleic acid sequence or an amino acid sequence" may mean that the polynucleotide or the polypeptide
  (i) essentially contains the specific nucleic acid sequence or amino acid sequence, or
  (ii) essentially consists of or contains a nucleic acid sequence or amino acid sequence having 60% or higher, 70% or higher, 80% or higher, 85% or higher, 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, or 99.9% or higher sequence identity with the specific nucleic acid sequence or amino acid sequence and retains a desired function. Herein, the desired function may be a CPC acylase function (e.g., catalytic activity of hydrolyzing CPC and/or producing 7-ACA from CPC) (for the amino acid sequence), or a function of coding for a protein having such a CPC acylase function.

As used herein, the term "sequence identity" refers to a degree of match between two nucleic acid sequences or between two amino acid sequences and may be expressed as a percentage (%). As for identity with nucleic acid sequences, for example, its determination can be made using the algorithm BLAST (see: Karlin and Altschul, Pro. Natl. Acad. Sci. USA, 90, 5873, 1993) or the algorithm FASTA developed by Pearson (see: Methods Enzymol., 183, 63, 1990). Based on the algorithm BLAST, programs called BLASTN or BLASTX have been developed.

As used herein, the term "amino acid residue at a specific position in the amino acid sequence of a protein (enzyme)" means an amino acid residue at a specific position in the amino acid sequence or an amino acid residue at a corresponding position in a homologous isotype protein and/or a heterologous protein having the same enzymatic activity as the protein.

When the first N-terminal amino acid residue in the amino acid sequence of a protein provided herein is methionine, it may be the residue contained in a natural state or may be synthesized in a recombinant process. Methionine, if absent at position 1 in the amino acid sequence of a protein, may be added as the first N-terminal residue during protein production in a recombinant manner.

As used herein, the term "about" is intended to encompass a numerical value that is identical to or numerical values that lie within the range of a certain variation of the following number, for example, within the range of a variation of ±0.5, ±0.4, ±0.3, ±0.2, ±0.1, ±0.05, or ±0.01 of the given value, but with no limitations thereto.

Below, a detailed description will be given of the present disclosure.

Mutant CPC Acylase

The present description provides a mutant CPC acylase with improved enzymatic activity. The mutant CPC acylase may result from the modification of imparting CPC acylase activity to conventional GI-7-ACA acylase.

GI-7-ACA acylase, used in the typical two-step enzymatic process (see the left reaction scheme in FIG. 1), is found in various soil microorganisms that are classified into five groups as in Table 1, below (classification of GI-7-ACA acylase) (Sonawane, Crit. Rev. Biotech. 26: 95-120, 2006):

TABLE 1

| Group | Representative Strain/Enzyme |
| --- | --- |
| Group I | *Pseudomonas* sp. A14 |
| Group II-A | *Bacillus lacteroporus* J1 |
| Group II-B | *Pseudomonas* sp. GK16 |
| Group II-C | *Pseudomonas* sp. SE83 Acyl |
| Group III | *Pseudomonas* sp. N176 |

On the basis of the classification in Table 1, the proteins within the same group are very similar in size, amino acid sequence, substrate specificity, and reactivity whereas large different characteristics are found between proteins in different groups.

GI-7-ACA acylases in Group III are disadvantageous in that their activity is easily inhibited by 7-ACA and inorganic salts and the enzymatic reaction stability is poor. Even the modified enzymes derived from GI-7-ACA acylases in Group III retain the drawbacks. In contrast, since GI-7-ACA acylases in Group II-B are free of the drawbacks of enzymes in Group III, modification of the GI-7-ACA acylase in Group II-B allows for the development of a mutant enzyme applicable advantageously to the one-step enzymatic process for production of 7-ACA (see the right reaction scheme in FIG. 1).

Most GI-7-ACA acylases are composed of an alpha-subunit, a spacer peptide, and a beta-subunit in that order. The basic gene (ga gene) used in the present disclosure is transcribed and translated into a polypeptide composed of an inactive single chain with a size of about 77 kDa. Then, the spacer peptide is processed by cleavage to form a dimer consisting of an 18 kDa alpha-subunit (SEQ ID NO: 3) and a 58 kDa beta-subunit (SEQ ID NO: 4).

Accordingly, the mutant CPC acylase of the present description may result from a modification made to GI-7-ACA acylase in Group II-B. The GI-7-ACA acylase in Group II-B may be a GI-7-ACA acylase derived from *Pseudomonas* sp. strain, for example, *Pseudomonas* sp. Strain GK16.

The *Pseudomonas* sp. GK16-derived, wild-type GI-7-ACA acylase (SEQ ID NO: 1) may be, for example, encoded by the nucleic acid molecule of SEQ ID NO: 2, or may be in the form of a dimer including an 18 kDa alpha subunit (SEQ ID NO: 3) and a 58-kDa beta-subunit (SEQ ID NO: 4) which are derived from a 77 kDa inactive monomeric chain including an alpha-subunit (e.g., SEQ ID NO: 3), a spacer peptide (e.g., SEQ ID NO: 5), and beta-subunit (e.g., SEQ ID NO: 4) in that order from the N terminus which is processed into the dimeric chain by cleaving the spacer peptide. Point mutation may be introduced into one or more residues on the alpha-subunit and/or beta-subunit to provide a mutant having CPC acylase activity.

An aspect provides a mutant CPC acylase, derived from a CPC acylase including an alpha-subunit and a beta-subunit, wherein the mutant CPC acylase includes a mutation by substitution of at least one (one, two, three, four, or five) selected from the group consisting of:
  (i) alanine at position 11 in the alpha-subunit of SEQ ID NO: 3 (A11α);
  (ii) glycine at position 24 in the alpha-subunit of SEQ ID NO: 3 (G24α);
  (iii) alanine at position 136 in the beta-subunit of SEQ ID NO: 4 (A136β);
  (iv) isoleucine at position 179 in the beta-subunit of SEQ ID NO: 4 (I179β); and
  (v) histidine at position 453 in the beta-subunit of SEQ ID NO: 4 (H453β)
  with an amino acid different from the corresponding original amino acid residue.

Another aspect provides a mutant CPC acylase, derived from a CPC acylase including an alpha-subunit and a beta-subunit, wherein the mutant CPC acylase includes a mutation by substitution of at least one (one, two, three, or four) selected from the group consisting of:
  (i) alanine at position 11 in the alpha-subunit of SEQ ID NO: 3 (A11α);
  (ii) glycine at position 24 in the alpha-subunit of SEQ ID NO: 3 (G24α);
  (iii) alanine at position 136 in the beta-subunit of SEQ ID NO: 4 (A136β); and
  (iv) isoleucine at position 179 in the beta-subunit of SEQ ID NO: 4 (I179β); and
  with an amino acid different from the corresponding original amino acid residue.

The amino acid for substitution for amino acid residues on the subunits may be selected from the group consisting of alanine (A, Ala), asparagine (N, Asn), threonine (T, Thr), glutamic acid (E, Glu), serine (S, Ser), valine (V, Val), isoleucine (I, Ile), leucine (L, Leu), aspartic acid (D, Asp), cysteine (C, Cys), glutamine (Q, Gln), methionine (M, Met), phenylalanine (F, Phe), proline (P, Pro), tryptophane (W, Trp), tyrosine (Y, Tyr), arginine (R, Arg), histidine (H, His), lysine (K, Lys), and glycine (G, Gly) and is different from the corresponding original amino acid residues.

In one embodiment, the mutant CPC acylase may include a mutation by at least one (one, two, three, four, or five) substitution selected from the group consisting of:
  (i-1) substitution of A11α in the alpha-subunit of SEQ ID NO: 3 with asparagine (N) (A11αN);
  (ii-1) substitution of G24α in the alpha-subunit of SEQ ID NO: 3 with aspartic acid (D) (G24αD);
  (iii-1) substitution of A136β in the beta-subunit of SEQ ID NO: 4 with threonine (T) (A136βT);
  (iv-1) substitution of I179β in the beta-subunit of SEQ ID NO: 4 with tyrosine (Y) (I179βY); and
  (v-1) substitution of H453β in the beta-subunit of SEQ ID NO: 4 with threonine (T) (H453βT).

In one embodiment, the mutant CPC acylase may include a mutation by at least one (one, two, three, or four) substitution selected from the group consisting of:
  (i-1) substitution of A11α in the alpha-subunit of SEQ ID NO: 3 with asparagine (N) (A11αN);
  (ii-1) substitution of G24α in the alpha-subunit of SEQ ID NO: 3 with aspartic acid (D) (G24αD);
  (iii-1) substitution of A136β in the beta-subunit of SEQ ID NO: 4 with threonine (T) (A136βT); and
  (iv-1) substitution of I179β in the beta-subunit of SEQ ID NO: 4 with tyrosine (Y) (I179βY).

In another embodiment, the mutant CPC acylase may further include, in addition to at least one (one, two, three, or four) selected from the group consisting of the amino acid substitutions (i) to (iv) (e.g., amino acid substitutions (i-1), (ii-1), (iii-1), and (iv-1)), a mutation by substitution of (v) histidine at position 453 in the beta-subunit of SEQ ID NO: 4 (H453β) with an amino acid different therefrom, for example, a mutation by (v-1) substitution of H453β in the beta-subunit of SEQ ID NO: 4 with threonine (T) (H453βT).

In another embodiment, the mutant CPC acylase may further include, in addition to the aforementioned amino acid substitution selected from the group consisting of the amino acid substitutions (i) to (v) (e.g., amino acid substitutions (i-1), (ii-1), (iii-1), (iv-1), and (v-1)), a mutation by at least one (one, two, three, four, or five, e.g., five) selected from the group consisting of the following substitutions in the beta-subunit of SEQ ID NO: 4:
  (vi) substitution of isoleucine at position 45 (I45β) with an amino acid different therefrom, for example, (vi-1) I45βV;
  (vii) substitution of phenylalanine at position 58 (F58β) with an amino acid different therefrom, for example, (vii-1) F58βV;
  (viii) substitution of tyrosine at position 153 (Y153β) with an amino acid different therefrom, for example, (viii-1) Y153βT;

(ix) substitution of phenylalanine at position 177 (F177β) with an amino acid different therefrom, for example, (ix-1) F177βL; and (x) substitution of valine at position 382 (V382β) with an amino acid different therefrom, for example, (x-1) V382βL.

The mutant CPC acylase including a mutation by amino acid substitutions (vi) to (x) (e.g., amino acid substitutions (vi-1), (vii-1), (viii-1), (ix-1), and (x-1)) retains the CPC acylase activity, but exhibits more enhanced CPC acylase activity and/or heat stability when further mutated by at least one (one, two, three, four, or five) selected from the group consisting of the amino acid substitutions (i) to (v) (e.g., amino acid substitutions (i-1), (ii-1), (iii-1), (iv-1), and (v-1)).

In a first embodiment, the mutant CPC acylase may include a mutation by the following substitution:
(i) substitution of the amino acid residue alanine at position 11 in the alpha-subunit of SEQ ID NO: 3 (A11α) with a different amino acid, for example, (i-1) A11αN.

In a second embodiment, the mutant CPC acylase may include a mutation by the following substitution:
(ii) substitution of the amino acid residue glycine at position 24 in the alpha-subunit of SEQ ID NO: 3 (G24α) with a different amino acid, for example, (ii-1) G24αD.

In a third embodiment, the mutant CPC acylase may include a mutation by the following substitution:
(iii) substitution of the amino acid residue alanine at position 136 in the beta-subunit of SEQ ID NO: 4 (A136β) with a different amino acid, for example, (iii-1) A136βT.

In a fourth embodiment, the mutant CPC acylase may include a mutation by the following substitution:
(iv) substitution of the amino acid residue isoleucine at position 179 in the beta-subunit of SEQ ID NO: 4 (I179β) with a different amino acid, for example, (iv-1) I179βY.

In a fifth embodiment, the mutant CPC acylase may include a mutation by the following substitution:
(v) substitution of the amino acid residue histidine at position 453 in the beta-subunit of SEQ ID NO: 4 (H453β) with a different amino acid, for example, (v-1) H453βT.

In a sixth embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN; and
(ii) substitution of the amino acid residue glycine at position 24 in the alpha-subunit of SEQ ID NO: 3 (G24α)) with a different amino acid, for example, (ii-1) G24αD.

In a seventh embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN; and
(iii) substitution of the amino acid residue alanine at position 136 in the beta-subunit of SEQ ID NO: 4 (A136β) with a different amino acid, for example, (iii-1) A136βT.

In an eighth embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN; and
(iv) substitution of the amino acid residue isoleucine at position 179 in the beta-subunit of SEQ ID NO: 4 (I179β) with a different amino acid, for example, (iv-1) I179βY In a ninth embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN; and
(v) substitution of the amino acid residue histidine at position 453 in the beta-subunit of SEQ ID NO: 4 (H453β) with a different amino acid, for example, (v-1) H453βT.

In a tenth embodiment, the mutant CPC acylase may include a mutation by the following substitutions:
(ii) substitution of the amino acid residue glycine at position 24 in the alpha-subunit of SEQ ID NO: 3 (G24α)) with a different amino acid, for example, (ii-1) G24αD; and
(iii) substitution of the amino acid residue alanine at position 136 in the beta-subunit of SEQ ID NO: 4 (A136β) with a different amino acid, for example, (iii-1) A136βT.

In an eleventh embodiment, the mutant CPC acylase may include a mutation by the following substitutions:
(ii) substitution of the amino acid residue glycine at position 24 in the alpha-subunit of SEQ ID NO: 3 (G24α)) with a different amino acid, for example, (ii-1) G24αD; and
(iv) substitution of the amino acid residue isoleucine at position 179 in the beta-subunit of SEQ ID NO: 4 (I179β) with a different amino acid, for example, (iv-1) I179βY.

In a twelfth embodiment, the mutant CPC acylase may include a mutation by the following substitutions:
(ii) substitution of the amino acid residue glycine at position 24 in the alpha-subunit of SEQ ID NO: 3 (G24α)) with a different amino acid, for example, (ii-1) G24αD; and
(v) substitution of the amino acid residue histidine at position 453 in the beta-subunit of SEQ ID NO: 4 (H453β) with a different amino acid, for example, (v-1) H453βT.

In a thirteenth embodiment, the mutant CPC acylase may include a mutation by the following substitutions:
(iii) substitution of the amino acid residue alanine at position 136 in the beta-subunit of SEQ ID NO: 4 (A136β) with a different amino acid, for example, (iii-1) A136βT; and
(iv) substitution of the amino acid residue isoleucine at position 179 in the beta-subunit of SEQ ID NO: 4 (I179β) with a different amino acid, for example, (iv-1) I179βY.

In a fourteenth embodiment, the mutant CPC acylase may include a mutation by the following substitutions:
(iii) substitution of the amino acid residue alanine at position 136 in the beta-subunit of SEQ ID NO: 4 (A136β) with a different amino acid, for example, (iii-1) A136βT; and (v) substitution of the amino acid residue histidine at position 453 in the beta-subunit of SEQ ID NO: 4 (H453β) with a different amino acid, for example, (v-1) H453βT.

In a fifteenth embodiment, the mutant CPC acylase may include a mutation by the following substitutions:
(iv) substitution of the amino acid residue isoleucine at position 179 in the beta-subunit of SEQ ID NO: 4 (I179β) with a different amino acid, for example, (iv-1) I179βY; and
(v) substitution of the amino acid residue histidine at position 453 in the beta-subunit of SEQ ID NO: 4 (H453β) with a different amino acid, for example, (v-1) H453βT.

In a sixteenth embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN;
(ii) substitution of the amino acid residue glycine at position 24 in the alpha-subunit of SEQ ID NO: 3 (G24α)) with a different amino acid, for example, (ii-1) G24αD; and
(iii) substitution of the amino acid residue alanine at position 136 in the beta-subunit of SEQ ID NO: 4 (A136β) with a different amino acid, for example, (iii-1) A136βT.

In a seventeenth embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN;
(ii) substitution of the amino acid residue glycine at position 24 in the alpha-subunit of SEQ ID NO: 3 (G24α)) with a different amino acid, for example, (ii-1) G24αD; and
(iv) substitution of the amino acid residue isoleucine at position 179 in the beta-subunit of SEQ ID NO: 4 (I179β) with a different amino acid, for example, (iv-1) I179βY.

In an eighteenth embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN;
(ii) substitution of the amino acid residue glycine at position 24 in the alpha-subunit of SEQ ID NO: 3 (G24α)) with a different amino acid, for example, (ii-1) G24αD; and
(v) substitution of the amino acid residue histidine at position 453 in the beta-subunit of SEQ ID NO: 4 (H453β) with a different amino acid, for example, (v-1) H453βT.

In a nineteenth embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN;
(iii) substitution of the amino acid residue alanine at position 136 in the beta-subunit of SEQ ID NO: 4 (A136β) with a different amino acid, for example, (iii-1) A136βT; and (iv) substitution of the amino acid residue isoleucine at position 179 in the beta-subunit of SEQ ID NO: 4 (I179β) with a different amino acid, for example, (iv-1) I179βY.

In a twentieth embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN;
(iii) substitution of the amino acid residue alanine at position 136 in the beta-subunit of SEQ ID NO: 4 (A136β) with a different amino acid, for example, (iii-1) A136βT; and
(v) substitution of the amino acid residue histidine at position 453 in the beta-subunit of SEQ ID NO: 4 (H453β) with a different amino acid, for example, (v-1) H453βT.

In a twenty-first embodiment, the mutant CPC acylase may include a mutation by the following substitutions:
(i) substitution of the amino acid residue alanine at position 11 in the alpha-subunit of SEQ ID NO: 3 (A11α)) with a different amino acid, for example, (i-1) A11αN;
(iv) substitution of the amino acid residue isoleucine at position 179 in the beta-subunit of SEQ ID NO: 4 (I179β) with a different amino acid, for example, (iv-1) I179βY; and
(v) substitution of the amino acid residue histidine at position 453 in the beta-subunit of SEQ ID NO: 4 (H453β)

In a twenty-second embodiment, the mutant CPC acylase may include a mutation by the following substitutions:
(ii) substitution of the amino acid residue glycine at position 24 in the alpha-subunit of SEQ ID NO: 3 (G24α)) with a different amino acid, for example, (ii-1) G24αD;
(iii) substitution of the amino acid residue alanine at position 136 in the beta-subunit of SEQ ID NO: 4 (A136β) with a different amino acid, for example, (iii-1) A136βT; and
(iv) substitution of the amino acid residue isoleucine at position 179 in the beta-subunit of SEQ ID NO: 4 (I179β) with a different amino acid, for example, (iv-1) I179βY.

In a twenty-third embodiment, the mutant CPC acylase may include a mutation by the following substitutions:
(ii) substitution of the amino acid residue glycine at position 24 in the alpha-subunit of SEQ ID NO: 3 (G24α)) with a different amino acid, for example, (ii-1) G24αD;
(iii) substitution of the amino acid residue alanine at position 136 in the beta-subunit of SEQ ID NO: 4 (A136β) with a different amino acid, for example, (iii-1) A136βT; and
(v) substitution of the amino acid residue histidine at position 453 in the beta-subunit of SEQ ID NO: 4 (H453β) with a different amino acid, for example, (v-1) H453βT.

In a twenty-fourth embodiment, the mutant CPC acylase may include a mutation by the following substitutions:
(iii) substitution of the amino acid residue alanine at position 136 in the beta-subunit of SEQ ID NO: 4 (A136β) with a different amino acid, for example, (iii-1) A136βT;

(iv) substitution of the amino acid residue isoleucine at position 179 in the beta-subunit of SEQ ID NO: 4 (I179β) with a different amino acid, for example, (iv-1) I179βY; and (v) substitution of the amino acid residue histidine at position 453 in the beta-subunit of SEQ ID NO: 4 (H453β) with a different amino acid, for example, (v-1) H453βT.

In a twenty-fifth embodiment, the mutant CPC acylase may include a mutation by the following substitutions:

(i) substitution of the amino acid residue alanine at position 11 in the alpha-subunit of SEQ ID NO: 3 (A11α)) with a different amino acid, for example, (i-1) A11αN;

(ii) substitution of the amino acid residue glycine at position 24 in the alpha-subunit of SEQ ID NO: 3 (G24α)) with a different amino acid, for example, (ii-1) G24αD;

(iii) substitution of the amino acid residue alanine at position 136 in the beta-subunit of SEQ ID NO: 4 (A136β) with a different amino acid, for example, (iii-1) A136βT; and (iv) substitution of the amino acid residue isoleucine at position 179 in the beta-subunit of SEQ ID NO: 4 (I179β) with a different amino acid, for example, (iv-1) I179βY.

In a twenty-sixth embodiment, the mutant CPC acylase may include a mutation by the following substitutions:

(i) substitution of the amino acid residue alanine at position 11 in the alpha-subunit of SEQ ID NO: 3 (A11α)) with a different amino acid, for example, (i-1) A11αN;

(ii) substitution of the amino acid residue glycine at position 24 in the alpha-subunit of SEQ ID NO: 3 (G24α)) with a different amino acid, for example, (ii-1) G24αD;

(iii) substitution of the amino acid residue alanine at position 136 in the beta-subunit of SEQ ID NO: 4 (A136β) with a different amino acid, for example, (iii-1) A136βT; and (v) substitution of the amino acid residue histidine at position 453 in the beta-subunit of SEQ ID NO: 4 (H453β) with a different amino acid, for example, (v-1) H453βT.

In a twenty-seventh embodiment, the mutant CPC acylase may include a mutation by the following substitutions:

(i) substitution of the amino acid residue alanine at position 11 in the alpha-subunit of SEQ ID NO: 3 (A11α)) with a different amino acid, for example, (i-1) A11αN;

(iii) substitution of the amino acid residue alanine at position 136 in the beta-subunit of SEQ ID NO: 4 (A136β) with a different amino acid, for example, (iii-1) A136βT;

(iv) substitution of the amino acid residue isoleucine at position 179 in the beta-subunit of SEQ ID NO: 4 (I179β) with a different amino acid, for example, (iv-1) I179βY; and (v) substitution of the amino acid residue histidine at position 453 in the beta-subunit of SEQ ID NO: 4 (H453β) with a different amino acid, for example, (v-1) H453βT.

In a twenty-eighth embodiment, the mutant CPC acylase may include a mutation by the following substitutions:

(i) substitution of the amino acid residue alanine at position 11 in the alpha-subunit of SEQ ID NO: 3 (A11α)) with a different amino acid, for example, (i-1) A11αN;

(ii) substitution of the amino acid residue glycine at position 24 in the alpha-subunit of SEQ ID NO: 3 (G24α)) with a different amino acid, for example, (ii-1) G24αD;

(iv) substitution of the amino acid residue isoleucine at position 179 in the beta-subunit of SEQ ID NO: 4 (I179β) with a different amino acid, for example, (iv-1) I179βY; and (v) substitution of the amino acid residue histidine at position 453 in the beta-subunit of SEQ ID NO: 4 (H453β) with a different amino acid, for example, (v-1) H453βT.

In a twenty-ninth embodiment, the mutant CPC acylase may include a mutation by the following substitutions:

(ii) substitution of the amino acid residue glycine at position 24 in the alpha-subunit of SEQ ID NO: 3 (G24α)) with a different amino acid, for example, (ii-1) G24αD;

(iii) substitution of the amino acid residue alanine at position 136 in the beta-subunit of SEQ ID NO: 4 (A136β) with a different amino acid, for example, (iii-1) A136βT.

(iv) substitution of the amino acid residue isoleucine at position 179 in the beta-subunit of SEQ ID NO: 4 (I179β) with a different amino acid, for example, (iv-1) I179βY; and (v) substitution of the amino acid residue histidine at position 453 in the beta-subunit of SEQ ID NO: 4 (H453β) with a different amino acid, for example, (v-1) H453βT.

In a thirtieth embodiment, the mutant CPC acylase may include a mutation by the following substitutions:

(i) substitution of the amino acid residue alanine at position 11 in the alpha-subunit of SEQ ID NO: 3 (A11α)) with a different amino acid, for example, (i-1) A11αN;

(ii) substitution of the amino acid residue glycine at position 24 in the alpha-subunit of SEQ ID NO: 3 (G24α)) with a different amino acid, for example, (ii-1) G24αD;

(iii) substitution of the amino acid residue alanine at position 136 in the beta-subunit of SEQ ID NO: 4 (A136β) with a different amino acid, for example, (iii-1) A136βT.

(iv) substitution of the amino acid residue isoleucine at position 179 in the beta-subunit of SEQ ID NO: 4 (I179β) with a different amino acid, for example, (iv-1) I179βY; and (v) substitution of the amino acid residue histidine at position 453 in the beta-subunit of SEQ ID NO: 4 (H453β) with a different amino acid, for example, (v-1) H453βT.

In another aspect, the mutant CPC acylase according to any of the first to the twenty-eighth embodiment may include an additional mutation by at least one (one, two, three, four, or five, e.g., five) selected from the group consisting of the following substitutions in the beta-subunit of SEQ ID NO: 4:

(vi) substitution of isoleucine at position 45 (I45β) with an amino acid different therefrom, for example, (vi-1) I45βV;

(vii) substitution of phenylalanine at position 58 (F58β) with an amino acid different therefrom, for example, (vii-1) F58βV;

(viii) substitution of tyrosine at position 153 (Y153β) with an amino acid different therefrom, for example, (viii-1) Y153βT;

(ix) substitution of phenylalanine at position 177 (F177β) with an amino acid different therefrom, for example, (ix-1) F177βL; and (x) substitution of valine at position 382 (V382β) with an amino acid different therefrom, for example, (x-1) V382βL.

Due to at least one (one, two, three, four, or five) substitution selected from the group consisting of the amino acid substitutions (i) to (v) (e.g., the amino acid substitutions (i-1), (ii-1), (iii-1), (iv-1), and (v-1)) described in the foregoing, the mutant CPC acylase provided in the present description may have improvement in enzymatic activity for CPC (acylase activity), thermal stability, or both of them, compared to CPC acylases which do not have any of the mutations (substitutions).

In greater detail, compared to the mutant CPC acylase including mutation by at least one the amino acid substitutions (vi) to (x) (e.g., amino acid substitutions (vi-1), (vii-1), (viii-1), (ix-1), and (x-1)), but neither of the amino acid substitutions (i) to (V) (e.g., amino acid substitutions (i-1), (ii-1), (iii-1), (iv-1), and (v-1)), the mutant CPC acylase provided herein may be improved:

in terms of enzymatic activity for CPC by about 2 times or higher, about 2.5 times or higher, about 3 times or higher, about 3.5 times or higher, about 4 times or higher, about 4.5 times or higher, about 5 times or higher, about 5.5 times or higher, about 6 times or higher, about 6.5 times or higher, about 7 times or higher, about 7.5 times or higher, about 8 times or higher, about 8.5 times or higher, about 9 times or higher, about 9.5 times or higher, about 10 times or higher, about 10.5 times or higher, about 11 times or higher, about 11.5 times or higher, about 12 times or higher, about 12.5 times or higher, about 13 times or higher, about 13.5 times or higher, about 14 times or higher, about 14.5 times or higher, or about 15 times or higher (no particular restrictions are imparted to the upper limit, for example, up to about 100 times, about 90 times, about 80 times, about 70 times, about 60 times, about 50 times, about 40 times, about 30 times, or about 25 times, but with no limitations thereto), and/or in terms of thermal stability by 1.05 times or greater, about 1.08 times or greater, about 1.1 times or greater, about 1.3 times or greater, about 1.5 times or greater, about 1.8 times or greater, about 2 times or greater, or about 2.3 times or greater (no particular restrictions are imparted to the upper limit, for example, up to about 10 times, about 9 times, about 8 times, about 7 times, about 6 times, about 5 times, about 4 times, about 3.5 times, or about 3 times, but with no limitations thereto).

In this regard, the term "enzymatic activity for CPC" refers to CPC acylase activity, and the unit for CPC acylase, accounting for enzymatic activity, is defined as the amount of the enzyme that catalyzes the conversion of one micromole of the substrate CPC per minute into 7-ACA. For instance, the acylase activity for CPC may mean the productivity of 7-ACA from CPC when the enzyme is allowed to react with the substrate CPC at 10° C. for 16-18 hours after being left at 25° C. for 2 hours and then at 10° C. for 1 hour in a cell lysis buffer (1.25 mg/mL lysozyme, 1.25 mM EDTA, and 0.375% (w/v) Triton X-100). The term "thermal stability" may mean the productivity of 7-ACA from CPC at a high temperature (about 40° C. or higher, e.g., about 45° C., about 50° C., about 55° C., or about 60° C.), for example, when the enzyme is allowed to react with the substrate CPC at 10° C. for 16-18 hours after being left at 25° C. for 2 hours and then at 55° C. for 1.5 hours in a cell lysis buffer (1.25 mg/mL lysozyme, 1.25 mM EDTA, and 0.375% (w/v) Triton X-100) (see Example 4 and Table 3).

In an embodiment, the mutant CPC acylase provided herein may be a non-naturally occurring enzyme, for example, produced in a recombinant manner or through chemical synthesis, but with no limitations thereto.

Nucleic Acid Molecule, Recombinant Expression Vector, and Recombinant Cell

Another aspect provides a nucleic acid molecule coding for the mutant CPC acylase described in the foregoing. The nucleic acid molecule may code for the full-length sequence of the mutant CPC acylase or may be a combination of nucleic acid molecules coding for the alpha-subunit and the beta-subunit in the mutant CPC, respectively.

Another aspect provides a recombinant vector carrying the nucleic acid molecule. The recombinant vector may be an expression vector that can express the nucleic acid molecule in a suitable host cell. The recombinant vector may be a single vector carrying a nucleic acid molecule coding for the full-length sequence of the mutant CPC acylase (for example, nucleic acid molecules coding for the alpha-subunit and the beta-subunit in one vector) or may be a combination of a first recombinant vector carrying a nucleic acid molecule coding for the alpha-subunit of the mutant CPC acylase and a second recombinant vector carrying a nucleic acid molecule coding for the beta-subunit of the mutant CPC acylase.

Another aspect provides a recombinant cell comprising the nucleic acid molecule and/or the recombinant vector. The recombinant cell may be obtained by introducing the nucleic acid molecule and/or recombinant vector into a suitable host cell.

In an embodiment, the recombinant cell may be an *Escherichia coli* strain, for example, *Escherichia coli* MC1061-pBC-TEP11 strain (accession number: KCTC 14821BP) resulting from introduction of the nucleic acid molecule into *Escherichia coli* MC1061, but with no limitations thereto.

The mutant CPC acylase may be produced by culturing the recombinant cell in a suitable medium under an appropriate condition.

In an embodiment, the mutant CPC acylase may be produced by culturing a host cell transformed with a recombinant vector carrying a nucleic acid molecule coding for the full-length sequence of the mutant CPC acylase in a suitable medium and condition. In another embodiment, the mutant CPC acylase may be produced by culturing a host cell transformed with a recombinant expression vector carrying a gene coding for the alpha-subunit of the mutant CPC acylase or a gene having a sequence functionally equivalent thereto and a host cell transformed with a recombinant expression vector carrying a gene coding for the beta-subunit of the mutant CPC acylase or a gene having a sequence functionally equivalent thereto in respective suitable media and conditions to afford corresponding CPC acylase subunit proteins, followed by combining the two subunit proteins in vitro.

The mutant CPC acylase prepared as in the foregoing according to the present disclosure may be used for producing the target product or may be purified before use. The isolation and purification of the mutant CPC acylase may be achieved using the already known properties of CPC acylase through various chromatographic protein separation methods as they are or in a manner modified for experimental purposes. Alternatively, the mutant CPC acylase can be purified by affinity chromatography using specific binding affinity, such as binding affinity between a histidine peptide and a nickel column component or between a cellulose binding domain (CBD) and a cellulose.

Also, the mutant CPC acylase of the present disclosure can be used in an immobilized state, but not in a free state. The mutant CPC acylase can be immobilized using a typical method known in the art. In this regard, a natural polymer such as cellulose, starch, dextran, agarose, etc.; a synthetic polymer such as polyacrylamide, polyacrylate, polymethacrylate, Eupergit C, etc.; or a mineral such as silica, bentonite, metal, etc. may be employed as a carrier. The mutant CPC acylase can be coupled to the carrier through a covalent bond, a hydrophobic bond, physical adsorption, microencapsulation, etc. In addition, the immobilization of the mutant CPC acylase in the carrier-enzyme conjugate form may be achieved through glutaraldehyde which forms covalent bonds between the cyanogen bromide of the carrier and the enzyme. Microbes containing the CPC acylase may be immobilized as they are, without separately purifying the enzyme. When such whole cell immobilization is employed, the cells may be punctured or a technique such as surface expression may be applied in order to increase the reactivity of the mutant CPC acylase contained therein.

In the coding regions of the nucleic acid sequences disclosed herein, various alterations or modifications may be made due to their codon degeneracy in consideration of the codons preferred by an organism in which the protein is to be expressed, provided that they do not change the amino acid sequence and/or function of the polypeptide expressed from the coding region.

The introduction of the nucleic acid molecule or vector may be carried out using a well-known transformation method appropriately selected by a person skilled in the art. As used herein, the term "transformation" means the introduction of a vector carrying a nucleic acid coding for a target protein (foreign protein) into a host cell in such a way that the protein encoded by the nucleic acid molecule is expressed in the host cell. So long as the transformed nucleic acid molecule is expressed in the host cell, it may be either integrated into the chromosome of the host cell and/or may exist extrachromosomally. Further, the nucleic acid molecule includes DNA and/or RNA encoding the target protein. The nucleic acid molecule may be introduced in any form as long as it can be introduced into the host cell and expressed therein. For example, the nucleic acid molecule may be introduced into the host cell via the form of an expression cassette that is a gene construct including all elements required for its autonomous expression. Typically, the expression cassette includes an expression regulatory element operatively linked to the nucleic acid molecule, such as a promoter, a transcriptional termination signal, a ribosome binding site, and/or a translation termination signal. The expression cassette may be in the form of a self-replicable expression vector. Also, the nucleic acid molecule as it is may be introduced into the host cell and operably linked to sequences required for expression in the host cell. As used herein, the term "operably linked" means a functional linkage between a nucleic acid molecule and an expression regulatory element (e.g., promoter) so as for the expression regulatory element to control (e.g., initiate) the transcription of the nucleic acid molecule encoding a target protein (foreign protein). The operative linkage may be carried out using a genetic recombination technique known in the art. By way of example, the linkage may be implemented by typical site-specific DNA cleavage and ligation, but is not limited thereto.

So long as it ensures the introduction of the nucleic acid molecule into a host cell (microorganism), any transformation may be used in the present disclosure. According to host cells, appropriate selection may be made of transformation techniques known in the art. Examples of the transformation methods known in the art include electroporation, calcium phosphate ($CaPO_4$) precipitation, calcium chloride ($CaCl_2$)) precipitation, microinjection, polyethylene glycol (PEG)-mediated uptake, DEAE-dextran-mediated gene transfer, cationic liposome-mediated gene transfer, lipofection, lithium acetate-DMSO method, heat shock, particle gun bombardment, silicon carbide whiskers, and sonication, but are not limited thereto.

The introduction (insertion) of the nucleic acid molecule into the genome (chromosome) of a host cell may be conducted using a known method appropriately selected by a person skilled in the art. For instance, the nucleic acid molecule may be introduced using at least one selected from the group consisting of an RNA-guided endonuclease system or CRISPR system (e.g., (a) RNA-guided endonuclease (i.e., Cas9 protein, etc.), a gene coding therefor, or a vector carrying the gene; and (b) guide RNA (i.e., single guide RNA (sgRNA), etc.)), a DNA coding therefor or a mixture including a vector carrying the DNA (e.g., a mixture of RNA-guided endonuclease protein and guide RNA, etc.), a complex (e.g., ribonucleoprotein (RNP)), and a recombinant vector (e.g., vector carrying both an RNA-guided endonuclease-encoding gene and a guide RNA-encoding DNA), but with no limitations thereto.

As used herein, the term "vector" refers to a DNA construct including a nucleotide sequence of a nucleic acid molecule coding for a target protein, which is operatively linked to an appropriate expression regulatory sequence to express the target protein in a suitable host cell. The regulatory sequence may include a promoter that can initiate transcription, an optional operator sequence for regulating the transcription, a sequence encoding a suitable mRNA ribosome binding site, and/or a sequence regulating the termination of transcription and/or translation. After being transformed into the suitable host cell, the vector may replicate or function independently of the host genome or may be integrated into the genome of the host cell.

The vector available in the present invention is not particularly limited as long as it is able to replicate in the host cell, and any vector known in the art may be used. Examples of conventional vectors may include a natural or recombinant plasmid, cosmid, virus, and bacteriophage. For instance, pWE15, M13, MBL3, MBL4, IXII, ASHII, APII, t10, t11, Charon4A, or Charon21A may be used as a phage vector or cosmid vector, and examples of plasmid vectors include pBC types (e.g., pBC-KS(+)), pBR types (e.g., pBR322, pBR325), pUC types (e.g., pUC118 and pUC119), pBluescriptII types, pGEM types, pTZ types, pCL types, pET types (e.g., pET-22b(+)), *Bacillus subtilis*-derived plasmids (e.g., pUB110, pTP5), plasmids derived from animal viruses such as retrovirus, adenovirus, Vaccinia virus, etc., plasmids derived from insect viruses such as Baculoviruses, but with no limitations thereto.

Any type of single-cell organisms typically used may be available as the host cell. For example, the host cell may be selected from the group consisting of prokaryotic microbes such as various bacteria (e.g., Clostridia spp. *Escherichia* spp., etc.) and eukaryotic microbes such as yeasts. Selection may be made of, for example, Clostridia spp. microorganisms (e.g., *Clostridium acetobutylicum, Clostridium beijerinckii, Clostridium saccharoperbutylacetonicum,* and *Clostridium saccharobutylicum*) and *Escherichia* spp. microorganisms (e.g., *Escherichia coli*), but with no limitations thereto.

The vector available herein may be a well-known expression vector and/or a vector for inserting a nucleic acid molecule into the chromosome. The insertion of a nucleic acid molecule into the chromosome of a host cell may be implemented by any method known in the art, for example, homologous recombination or a CRISPR system, but with no limitations thereto. The vector may further include a selection marker for indicating insertion into the chromosome. The selection marker is adapted to select transformed cells, that is, to determine whether the polynucleotide is inserted or not, and may be selected from genes leading to selectable phenotypes such as drug resistance, auxotrophy, resistance to cytotoxic agents, or expression of surface proteins. In the presence of a selective agent, only the cells expressing the selection marker are alive or exhibit a different expression trait and thus can be selected.

Production of 7-Aminocephalosporanic Acid (7-ACA)

Another aspect of the present description provides a composition for producing 7-aminocephalosporanic acid (7-ACA) or a salt thereof, the composition including at least one selected from the group consisting of the mutant CPC acylase described in the foregoing, a nucleic acid sequence coding for the mutant CPC acylase, a recombinant expression vector carrying the nucleic acid sequence, a recombinant cell comprising the nucleic acid sequence and/or the recombinant expression vector, and a culture of the recombinant cell.

Another aspect provides a use of at least one selected from the group consisting of the mutant CPC acylase described in the foregoing, a nucleic acid sequence coding for the mutant CPC acylase, a recombinant expression vector carrying the nucleic acid sequence, a recombinant cell comprising the nucleic acid sequence and/or the recombinant expression vector, and a culture of the recombinant cell for producing 7-ACA or a salt thereof.

Another aspect provides a method for producing 7-ACA or a salt thereof, using at least one selected from the group consisting of the mutant CPC acylase described in the foregoing, a nucleic acid sequence coding for the mutant CPC acylase, a recombinant expression vector carrying the nucleic acid sequence, a recombinant cell comprising the nucleic acid sequence and/or the recombinant expression vector, and a culture of the recombinant cell.

Another aspect provides a method for producing a compound of Chemical Formula 2 or a salt thereof, the method comprising a step of contacting at least one selected from the group consisting of the mutant CPC acylase described in the foregoing, a nucleic acid sequence coding for the mutant CPC acylase, a recombinant expression vector carrying the nucleic acid sequence, a recombinant cell comprising the nucleic acid sequence and/or the recombinant expression vector, and a culture of the recombinant cell with a compound of Chemical Formula 1 or a salt thereof:

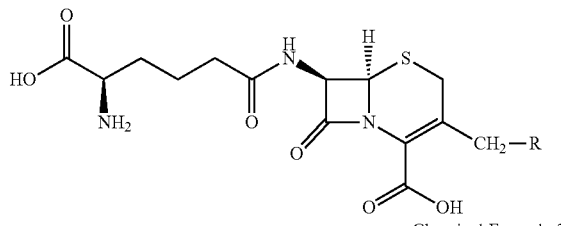

Chemical Formula 1

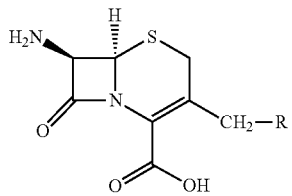

Chemical Formula 2

(wherein, R is acetoxy (—OCOCH$_3$), hydroxy (—OH), or hydrogen (—H) group).

The salt may be any type of pharmaceutically acceptable salts. For example, alkali metal salts (e.g., sodium salts, potassium salts, lithium salts, etc.) may be used, but with no limitations thereto. In an embodiment, the compound of Chemical Formula 1 may be a CPC substrate compound and the compound of Chemical Formula 2 may be 7-ACA.

The method, provided herein, for producing a compound of Chemical Formula 2 or a salt thereof, for example, 7-ACA or a salt thereof may be a one-step method for producing 7-ACA or a salt thereof directly from CPC.

That is, the method may not include a step of treating CPC with D-amino acid oxidase. Through the enzymatic reaction of D-amino acid oxidase, CPC is converted into glutaryl-7-aminocephalosporanic acid (hereinafter referred to as "GI-7-ACA") during which hydrogen peroxide is also generated and attacks the substrate (CPC), the reaction product (GI-7-ACA), and D-amino acid oxidase, thus lowering the production yield. In contrast, the method provided herein does not include the step of treating CPC with D-amino acid oxidase, but produces 7-ACA or a salt thereof directly from CPC, thereby solving the problems.

The recombinant cell is a strain for producing the mutant CPC acylase.

The compound of Chemical Formula 2 can be prepared by contacting the compound of Chemical Formula 1 with the mutant CPC acylase which may be within the mutant CPC acylase-producing strain or a culture of the mutant CPC acylase-producing strain (e.g., a liquid phase, semi-solid phase, or solid phase culture, or a culture of a concentrate or dried form) or in the form of a composition or may be in an isolated state or an immobilized state. The contact between the mutant CPC acylase and the compound of Chemical Formula 1 may be conducted in water or an aqueous solution (e.g., buffer). In this regard, conditions for the enzymatic reaction include a concentration of 1-500 mM for the compound of Chemical Formula 1, an amount of 0.1-100 U/mL for the mutant CPC acylase, a pH of 7-10 for the reaction mixture, a reaction time of 0.1-24 hours, and a reaction temperature of 4-40° C., but are not limited thereto. The compound of Chemical Formula 2 produced through the enzymatic reaction can be separated and/or purified by a typical method.

In addition, the compound of Chemical Formula 2 can be prepared in a cell through contact between the mutant CPC acylase and the compound of Chemical Formula 1. A recombinant expression vector carrying the mutant CPC acylase-encoding gene or a derivative having a functionally equivalent sequence is introduced into a strain able to biosynthesize the compound of Chemical Formula 1, such as *E. coli* or *Acremonium chrysogenum*, and the resulting transformant is cultured in a suitable medium under a proper condition, during which the biosynthesized compound of Chemical Formula 1 is spontaneously contacted with the mutant CPC acylase within the transformant to prepare the compound of Chemical Formula 2.

Effect of the Invention

Provided herein is a mutant enzyme for producing 7-ACA, which is used as a raw material for cephalosporins. More specifically, a cephalosporin C acylase mutated to increase in enzymatic activity for cephalosporin C and/or thermal stability and a 7-ACA production method using same are provided, whereby the mutant CPC acylase of the present disclosure exhibits about 5-fold, for example, about 5- to about 21-fold higher enzymatic activity for CPC substrate and about 2.5-fold higher thermal activity than the conventional mutant CPC acylase (PM2). In addition, the technique of the present disclosure is a one-step process enjoying the advantage of effectively producing 7-ACA directly from CPC.

EXAMPLES

Figure 1:
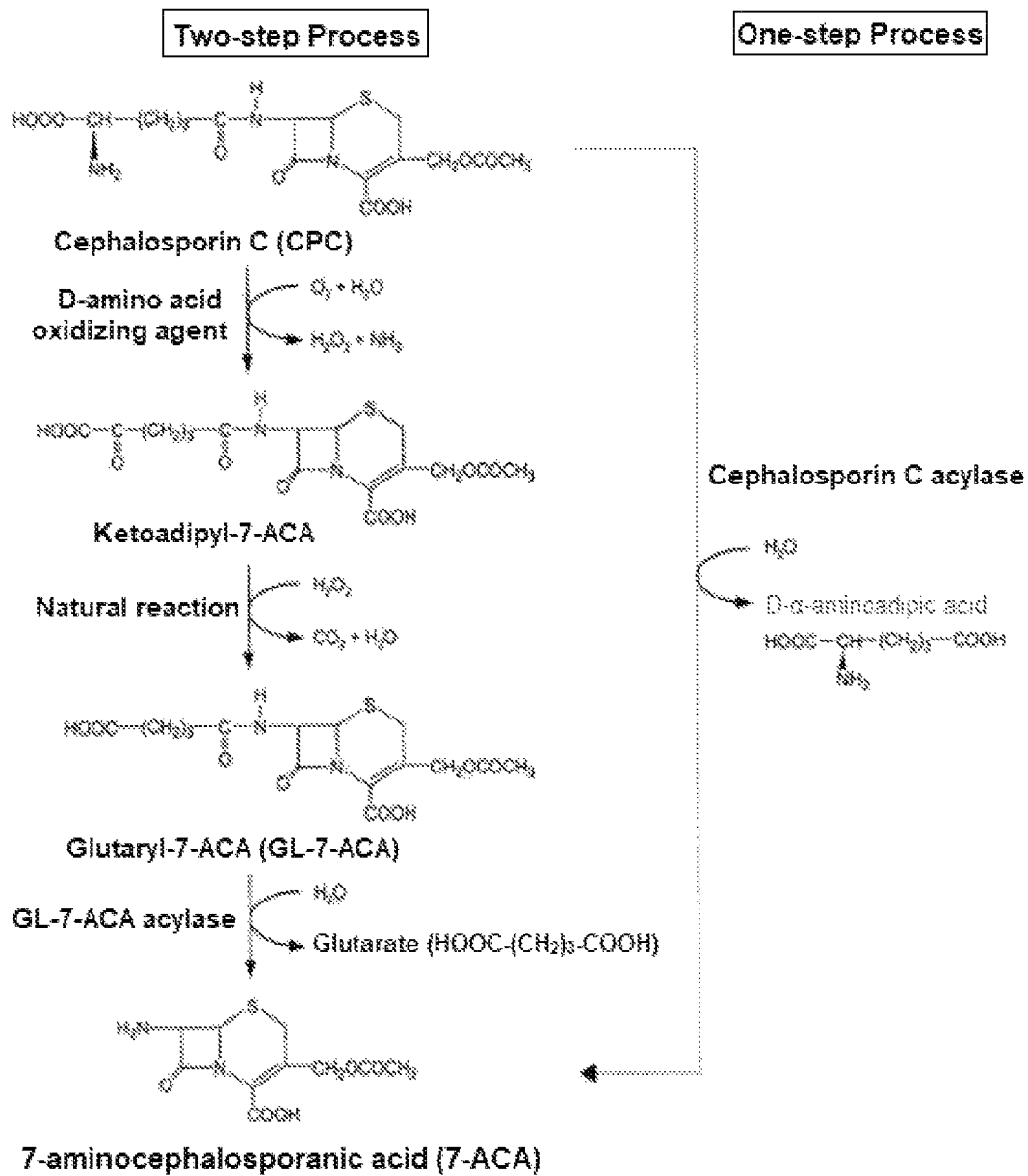
FIG. 1 is a schematic view showing a one-step and a two-step enzymatic process for producing 7-ACA from CPC.
Figure 2:
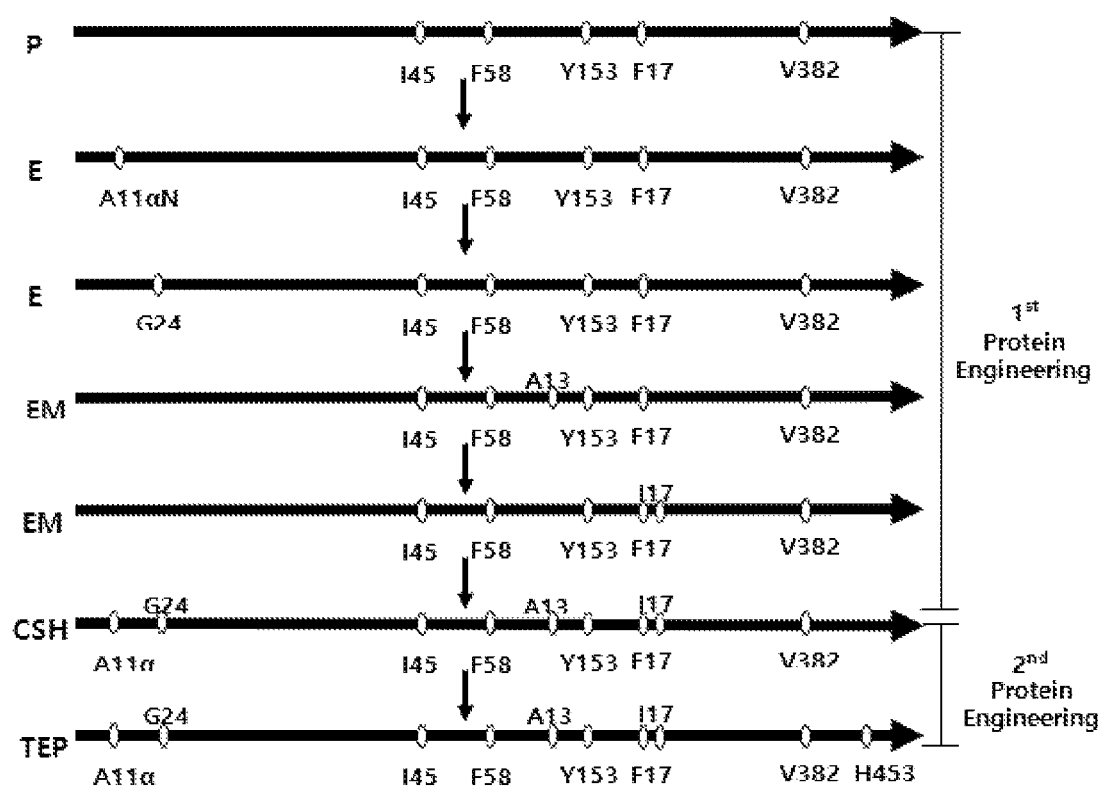
FIG. 2 is a schematic view showing a process of preparing a mutant CPC acylase according to an embodiment.

A better understanding of the present disclosure may be obtained in light of the following examples which are set forth to illustrate, but are not to be construed to limit, the present disclosure. It is apparent to those skilled in the art that the Examples described below may be modified without departing from the essential gist of the disclosure.

Example 1: Mutant CPC Acylase Preparation and Activity Measurement 1-1. Construction of pBC-PM2 Plasmid To develop a mutant CPC acylase with improved enzymatic activity, a *Pseudomonas* sp. GK16 strain (Matsuda et. al., J. Bacteriol. 163: 1222-1228, 1985)-derived glutaryl amidase (GA) mutant (SEQ ID NO: 6)-encoding gene (hereinafter referred to as "pm gene"; SEQ ID NO: 7) was used as a base gene. The glutaryl amidase (GA) mutant (hereinafter referred to as "PM2 mutant") is a single chain polypeptide in which the wild-type alpha-subunit (SEQ ID NO: 3), the spacer (SEQ ID NO: 5), and a quintuple mutant (I45βV/F58βV/Y153βT/F177βL/V382βL; SEQ ID NO: 8) of the beta-subunit (SEQ ID NO: 4) are linked through peptidyl bonds in that order from the N terminus (refer to Korean Patent No. 10-2014-0094150 A; incorporated herein by reference in its entirety).

The pm gene was used as a precursor herein, and is expressed into a single chain polypeptide (SEQ ID NO: 6) in which the wild-type alpha-subunit of SEQ ID NO: 3 and the mutant beta-subunit of SEQ ID NO: 8 are linked to each other through the space of SEQ ID NO: 5 by peptidyl bonds, and then is developed into a mature active dimeric form consisting of the alpha-subunit and the beta-subunit through an autocatalytic process within the cell. The pm gene of SEQ ID NO: 7 was inserted into the pBC-KS (+) vector (Stratagene, USA) at the sites recognized by XbaI and NotI restriction enzymes recognition site to construct a pBC-PM2 plasmid for expressing the PM2 mutant. A concrete construction method is as follows.

The pm gene DNA product (about 2.1 kb in size) was digested with the restriction enzymes XbaI and NotI and purified using a purification kit (QIAquick Gel Extraction Kit; QIAGEN, Germany) to prepare a DNA to be inserted. Separately, a pBC KS(+) vector (Stratagene, USA) was also cleaved with XbaI and NotI and dephosphorylated with CIP (Calf Intestinal Alkaline Phosphatase) to give a vector DNA. The prepared DNA to be inserted was ligated to the vector DNA at 16° C. for 12-16 hours in the presence of T4 DNA ligase (New England Biolabs, Sweden) and the ligation mixture was transformed into *E. coli* MC1061 by electroporation. The strain was spread on LB agar plates containing 20 μg/mL chloramphenicol antibiotic and statically incubated overnight at 30° C. to select transformants. The plasmid was isolated from the selected transformant and subjected to base sequencing to identify the nucleotide sequence of the DNA insert. The resulting pBC-PM2 plasmid carrying the pm gene having the nucleotide sequence of SEQ ID NO: 7 was designed to express a PM2 mutant protein including the quintuple mutant (I45βV/F58βV/Y153βT/F177βL/V382βL) of the beta-subunit.

1-2. Preparation of Enzyme Solution

The pBC-PM2 plasma-containing recombinant *E. coli* transformant prepared in Example 1-1 was assayed for productivity of CPC (cephalosporin C) acylase. For use in this assay, a CPC acylase coenzyme solution was prepared as follows: the *E. coli* transformant was inoculated into 3 mL of an LB broth (1% Bacto-tryptone, 0.5% yeast extract, 0.5% NaCl) containing 20 μg/mL chloramphenicol and cultured at 30° C. for 16 hours while agitating at 200 rpm. Thereafter, 350 μL of the culture was inoculated into 35 mL of a fresh LB medium containing 20 μg/mL chloramphenicol and cultured at 25° C. for 48 hours while agitating at 200 rpm. The resulting culture was centrifuged (4° C., 8000 rpm, 10 min) to recover the cell mass which was then washed once with a 0.1M potassium phosphate buffer (pH 8.0). The cells were suspended in 35 mL of the same buffer, lysed at 4° C. for 10 min by sonication (Vibra Cell VC750, Sonics & Materials Inc, USA), followed by centrifugation at 4° C. and 13,500 rpm for 20 min. The supernatant thus formed was used as a mutant CPC acylase coenzyme solution. Below, the activity and thermal stability of CPC acylase were assayed using the enzyme solutions prepared from each strain according to the method described above.

1.3. Assay for CPC Acylase Activity

The activity of the CPC acylase prepared in Example 1.2 was measured using the Park et al. method (Park et al., Kor. J. Appl. Microbiol. Biotechnol. 23: 559-564, 1995), with a modification thereto, as follows.

The CPC substrate (purity 90%; Hayao, China) was dissolved at a concentration of 40 mM in a 0.1 M potassium phosphate buffer (pH 8.0) to give a substrate solution. To 20 μL of the CPC substrate solution was added 20 μL (microliter) of the enzyme solution prepared in Example 1.2. After the enzymatic reaction at 37° C. for 5 min, the reaction was terminated by adding 200 μL of 50 mM NaOH-20% (w/v) glacial acetic acid (1:2, NaOH: glacial acetic acid, by volume). Then, centrifugation was conducted at 13000 rpm for 5 min and 200 µL of the supernatant thus formed was added with 40 µL of a solution of 0.5% (w/v) PDAB (p-dimethylaminobenzaldehyde; Sigma, USA) in methanol. Following the reaction for 10 min, absorbance was read at 415 nm. Quantitation was made by projecting the absorbance to a calibration curve for reference material. In this regard, one unit was defined as is defined as the amount of the enzyme that catalyzes the conversion of one micromole of the CPC substrate per minute into 7-aminocephalosporanic acid (7-ACA). Separately, the specific activity for CPC substrate was expressed as the activity unit of the enzyme per milligram of the total protein which was quantitated in the enzyme solution by the Bradford method (Bradford, M., Anal. Biochem. 72: 248-254, 1976).

As a result of the assay for CPC acylase activity, the recombinant *E. coli* MC1061 (pBC-PM2) strain prepared in Example 1.1 was measured to express the CPC acylase at a productivity of about 1300 units/L.

Example 2: Preparation and Selection of CPC Acylase with High Activity 2.1. Construction of Primary Library by Error-Prone PCR To prepare a mutant CPC acylase having improved CPC acylase activity, random mutations were artificially made to the nucleotide sequence of the pm gene described in Example 1.1. To this end, error-prone PCR was conducted to construct a library of mutants. Concrete processes of constructing a library of mutants are as follows.

Error-prone PCR was carried out using a Diversity PCR Random Mutagenesis kit (Clontech, USA) to cause 1-2 mutations per 1,000 bp. The PCR reaction mixture contained 1 ng/µL pBC-PM2 plasmid (Example 1.1) as a substrate DNA, 10 pmol of a T3 primer (SEQ ID NO: 15), 10 pmol of a T7 primer (SEQ ID NO: 16), 2 mM of dGTP, 50× Diversity dNTP mix, 10× TITANIUM Taq buffer, and TITANIUM Taq polymerase in a total volume of 50 µL. The PCR reaction condition was as follows: PCR was initiated by pre-denaturation at 95° C. for 2 min and subjected to 18 cycles of denaturation at 95° C. for sec, annealing at 52° C. for 30 sec, and extension at 68° C. for 3 min, followed by post-extension at 68° C. for 5 min. In this condition, amplification by the error-prone PCR resulted in a mutant DNA fragment with a size of about 2.1 kb.

The mutant genes obtained by error-prone PCR in the condition, that is, 2.1-kb PCR products were cut with the restriction enzymes XbaI and NotI and then purified using a purification kit (QIAquick Gel Extraction Kit; QIAGEN, Germany) to prepare a DNA to be inserted. Separately, a pBC-KS(+) vector (Stratagene, USA) was also cleaved with XbaI and NotI and dephosphorylated with CIP to give a vector DNA. The prepared DNA to be inserted was ligated to the vector DNA at 16° C. for 12-16 hours in the presence of T4 DNA ligase (New England Biolabs, Sweden) and the ligation mixture was transformed into *E. coli* MC1061 by electroporation. The strain was spread on LB agar plates containing 20 µg/mL chloramphenicol antibiotic and statically incubated overnight at 30° C. to construct a random mutant library.

From the mutant library, mutant CPC acylases with improved reactivity for CPC substrate were screened as follows.

*E. coli* MC1061 transformants including the mutant CPC acylase genes into which the additional mutations were introduced as described above were inoculated into 96-well plates, each well containing 160 µL of an LB broth supplemented with chloramphenicol, and was cultured at 30° C. for 60-70 hours while agitation at 165 rpm. Thereafter, 20 µL of the culture taken from each well was transferred to new 96-well plates and added with 105 µL of a cell lysis buffer (1.25 mg/mL lysozyme, 1.25 mM EDTA, and 0.375% (w/v) Triton X-100), followed by incubation at 25° C. for 2 hours and then at 10° C. for one hour. To each well, 125 µL of a substrate solution of 50 mM CPC in a 25 mM potassium phosphate buffer (pH 8.0) was added to perform a hydrolysis reaction on the CPC substrate at 10° C. for 16-18 hours. Following the hydrolysis reaction, 40 µL of the supernatant was transferred to each well of new 96-well plates. The enzymatic reaction was terminated with 100 µL of a reaction stop solution (acetic acid: 250 mM NaOH, 2:1), added with 30 µL of a color development reagent (0.5% (w/v) PDAB in methanol), and left at room temperature for 10 min. Subsequently, absorbance was read on a 96-well plate reader at 415 nm, which is the wavelength indicative of the formation of 7-ACA, thereby screening mutants having improved activity for the CPC substrate.

As a result, selection was made of four mutants (EM5, EM9, EM17, and EM42) which had improved CPC acylase activity compared to PM2 (including I45βV/F58βV/Y153βT/F177βL/V382βL mutations), from about 30,000 mutants. Base sequencing of the genes of the mutants revealed the substitution of the amino acid residue A11α (alanine at position 11 in the alpha-subunit) with asparagine (A11αN) in EM5 mutant enzyme, substitution of the amino acid residue G24α with aspartic acid (A11αD) in EM9 mutant enzyme, the substitution of the amino acid residue A136β (alanine at position 136 in the beta-subunit) with threonine (A136βT) in EM17 mutant enzyme, and the substitution of the amino acid residue I179β with tyrosine (I179βY) in EM42 mutant enzyme.

2.2. Construction of Secondary Mutant Library by Site-Directed Mutagenesis (DNA Shuffling)—Selection of Modified Strain (CSH17)

To further increase CPC acylase activity, site-directed mutant libraries for the four amino acid residues (A11αN, G24αD, A136βT, and I179βY) were constructed on the basis of the activity of the modified strains obtained by the error-prone PCR in Example 2.1.

In brief, to construct mutant libraries for A11α and G24α, PCR was performed using M13-R primer (SEQ ID NO: 17) and SH24α-R primer (SEQ ID NO: 18) on the substrates PM2 and EM5 to obtain PCR products about 240 bp in size. Mutant libraries for G24α, A136β, and I179β were constructed by performing PCR using SH24α-F primer (SEQ ID NO: 19) and SH179β-R primer (SEQ ID NO: 20) on the substrates PM2 and EM17 to afford PCR products about 975 bp in size. For a mutant library for I179β, PCR was conducted using SH179β-F primer (SEQ ID NO: 21) and M13-F primer (SEQ ID NO: 22), with PM2 serving as a template, to obtain a PCR product about 1,120 bp in size.

In a final volume of 100 µL of the PCR reaction solution, a corresponding substrate DNA, primers, a pfu-x buffer, a dNTPs mix, and a pfu-x polymerase were contained. PCR was initiated by pre-denaturation at 95° C. for 2 min and subjected to 18 cycles of denaturation at 95° C. for 30 sec, annealing at 52° C. for 30 sec, and extension at 68° C. for 3 min, followed by post-extension at 68° C. for 5 min.

The PCR products having sizes of about 240 bp, about 975 bp, and about 1,120 bp, thus obtained by PCR in the condition were mixed and subjected to PCR using T3 primer (SEQ ID NO: 15) and T7 primer (SEQ ID NO: 16) to amplify a 2.1-kb DNA fragment having multiple mutations. The 2.1-kb PCR product was inserted into a pBC-KS(+)

vector DNA in the same manner as in Example 2.1 and then transformed into *E. coli* MC1061 to construct a site-directed mutant library.

In the site-directed mutant library, search was made for mutant CPC acylase having increased activity for CPC substrate in the same manner as in Example 2.1. As a result, a quadruple mutant (A11αN/G24αD/A136βT/I179βY) higher in CPC acylase activity than PM2 was selected in the same manner as in Example 2.1 and named CSH17. The CSH17 mutant enzyme (SEQ ID NO: 9) includes the alpha subunit of SEQ ID NO: 10 and the beta subunit of SEQ ID NO: 11.

Example 3: Preparation and Selection of Mutant Having Increased Thermal Stability Necessary for Enzymatic Stability—Construction of Tertiary is Mutant Library by Error-Prone PCR—Selection of Modified Strain TEP11

To further increase the thermal stability of the modified strain CSH17 prepared in Example 2.2, a CSH17 (SEQ ID NO: 9)-encoding DNA was used as a template DNA for constructing an error-prone mutant library in the same manner as in Example 2.1.

In the mutant library, search was made for mutant CPC acylase with increased thermal stability in the same manner as in Example 2.1, except for the thermal treatment condition. In brief, error-prone PCR (see Example 2.1) was conducted on a CSH17 (SEQ ID NO: 9)-encoding DNA as a template, to construct a random mutant library. The resulting *E. coli* MC1061 transformant which included a mutant CPC acylase gene having the mutation introduced thereinto was inoculated into 96-well plates, each well containing 160 µL of an LB broth supplemented with chloramphenicol and then cultured at 30° C. for 60-70 hours while agitating at 165 rpm. Thereafter, 20 µL of the culture taken from each well was transferred to new 96-well plates and added with 105 µL of a cell lysis buffer (1.25 mg/mL lysozyme, 1.25 mM EDTA, and 0.375% (w/v) Triton X-100), followed by incubation at 25° C. for 2 hours and then at 55° C. for 1.5 hours for heat treatment. To each well, 125 µL of a substrate solution of 50 mM CPC in a 25 mM potassium phosphate buffer (pH 8.0) was added to perform a hydrolysis reaction on the CPC substrate at 10° C. for 16-18 hours.

In the error-prone mutant library thus constructed, search was made for mutant CPC acylase having increased thermal stability. As a result, a strain having a mutation by substitution of H453β with threonine (H453βT) plus the CSH17 mutation (quadruple mutation A11αN/G24αD/A136βT/I179βY) was observed to exhibit high CPC acylase activity and remarkably increased thermal stability, compared to the CSH17 mutant, and named TEP11. TEP11 (SEQ ID NO: 12) includes the alpha subunit of SEQ ID NO:13 and the beta subunit of SEQ ID NO: 14.

Below, representative mutants of Examples 2 and 3 were assayed for CPC acylase activity and thermal stability.

Example 4: Assay for Activity and Thermal Stability of CPC Acylase Mutant

The CPC acylase mutants of Examples 2 and 3 were assayed for enzymatic activity and thermal stability in the same manners as in Examples 1.3 and 3, respectively. the results are summarized in Tables 2 and 3 (activity or thermal stability of mutant enzymes are expressed as relative values (folds) to that of PM2).

TABLE 2

Mutated Residue in Mutant CPC Acylase and Comparison of Enzymatic Activity of CPC Acylase

| Mutant Enz. | Mutant Residue | Relative activity for CPC substrate (fold) |
|---|---|---|
| PM2 | I45βV/F58βV/Y153βT/F177βL/V382βL | 1.0 |
| EM5 | A11αN/I45βV/F58βV/Y153βT/F177βL/V382βL | 6.3 |
| EM9 | G24αD/I45βV/F58βV/Y153βT/F177βL/V382βL | 4.5 |
| EM17 | I45βV/F58βV/A136βT/Y153βT/F177βL/V382βL | 5.2 |
| EM42 | I45βV/F58βV/Y153βT/F177βL/I179βY/V382βL | 6.9 |
| CSH17 | A11αN/G24αD/I45βV/F58βV/A136βT/Y153βT/F177βL/I179βY/V382βL | 15.7 |
| TEP11 | A11αN/G24αD/I45βV/F58βV/A136βT/Y153βT/F177βL/I179βY/V382βL/H453βT | 20.8 |

TABLE 3

Mutated Residue in Mutant CPC Acylase and Comparison of Thermal Stability of CPC Acylase

| Mutant Enz. | Mutant Residue | Relative activity for thermal stability (fold) |
|---|---|---|
| PM2 | I45βV/F58βV/Y153βT/F177βL/V382βL | 1.0 |
| CSH17 | A11αN/G24αD/I45βV/F58βV/A136βT/Y153βT/F177βL/I179βY/V382βL | 1.1 |
| TEP11 | A11αN/G24αD/I45βV/F58βV/A136βT/Y153βT/F177βL/I179βY/V382βL/H453βT | 2.4 |

Among the mutant enzymes, TEP11 mutant enzyme was observed to exhibit the highest activity and thermal stability. A pBC-TEP11 plasmid carrying a gene coding for the TEP11 mutant enzyme was transformed into an *E. coli* MC1061 strain which was then named "*Escherichia coli* MC1061-pBC-TEP11" and deposited with the Korean Collection for Type Cultures, located at Jeongeup-si. Jeollabuk-do, Korea, on Dec. 13, 2021 (accession number: KCTC 14821BP).

Example 5: Comparison of Enzymatic Activity and Thermal Stability of CPC Acylase Mutants (vs. Wild-Type CPC Acylase)

Mutant enzymes in which the five CPC acylate mutations (A11αN, G24αD, A136βT, I179βY, and H453βT) selected in Examples 2 and 3 were introduced into wild-type CPC acylase were assayed for enzymatic activity and thermal stability.

The mutants respectively including the five CPC acylase mutations (A11αN, G24αD, A136βT, I179βY, and H453βT) were prepared by site-directed mutagenesis.

Briefly, the five CPC acylase mutants (A11αN, G24αD, A136βT, I179βY, and H453βT) were prepared by PCR, with the wild-type CPC acylase (SEQ ID NO: 1) serving as a template. The primers in PCR are summarized in Table 4, below.

TABLE 4

| Mutant Enz. GA | Mutant residue WT | F Primer | R Primer |
|---|---|---|---|
| SM7 | I179βY | GTTCCGA CCTTTAA CTATGTT TATGCTG ATCGTG (SEQ ID NO: 23) | CACGATC AGCATAA ACATAGT TAAAGGT CGGAAC (SEQ ID NO: 24) |
| SM10 | G24αD | GAAATCC TGTGGGA TGACTAT GGTGTTC CGCATAT C (SEQ ID NO: 25) | GATATGC GGAACAC CATAGTC ATCCCAC AGGATTT C (SEQ ID NO: 26) |
| SM25 | A136βT | CGTGCTG ATGGTAC CACCGTT GCTGTTC GTGTTG (SEQ ID NO: 27) | CAACACG AACAGCA ACGGTGG TACCATC AGCACG (SEQ ID NO: 28) |
| SM43 | A11αN | CCGCAGG CTCCGAT CAATGCT TATAAAC CGCGTAG C (SEQ ID NO: 29) | GCTACGC GGTTTAT AAGCATT GATCGGA GCCTGCG G (SEQ ID NO: 30) |
| SM52 | H453βT | GTGCGTA CCCCGGT TACGGGT GAAACCT GGGTTGC (SEQ ID NO: 31) | GCAACCC AGGTTTC ACCCGTA ACCGGGG TACGCAC (SEQ ID NO: 32) |

In a final volume of 100 μL of the PCR reaction solution, a corresponding substrate DNA, primers, a pfu-x buffer, a dNTP mix, and a pfu-x polymerase were contained. PCR was initiated by pre-denaturation at 95° C. for 2 min and subjected to 18 cycles of denaturation at 95° C. for 30 sec, annealing at 52° C. for 30 sec, and extension at 68° C. for 3 min, followed by post-extension at 68° C. for 5 min. The PCR product with a size of 2.1 kb, obtained in the condition, was inserted into a pBC-KS(+) vector DNA in the same manner as in Example 2.1 and transformed into *E. coli* MC1061 to give a site-directed mutant strain. For comparison, a recombinant strain was prepared by introducing wild-type CPC acylase (SEQ ID NO: 1) into *E. coli* MC1061.

The five CPC acylase mutant strains prepared above were assayed for enzymatic activity for CPC substrate and thermal stability with reference to the methods of Example 1.3 (enzymatic activity) and Example 3 (thermal stability, measured using the enzyme solution left at 40° C. for 30 min), in comparison with the wild-type strain (SEQ ID NO: 1). The results are given in Table 5, below.

TABLE 5

| Mutant Enz. | Mutant Residue | Relative activity for CPC substrate (fold) | Relative activity for thermal stability (fold) |
|---|---|---|---|
| GA | Wild type | 1.00 | 1.00 |
| SM7 | I179βY | 6.20 | 1.05 |
| SM10 | G24αD | 3.40 | 1.01 |
| SM25 | A136βT | 2.85 | 0.98 |
| SM43 | A11αN | 4.70 | 1.07 |
| SM52 | H453βT | 5.60 | 2.40 |

As can be seen in TABLE 5, the respective mutants having the five CPC acylase mutations (A11αN, G24αD, A136βT, I179βY, and H453βT) singly introduced thereinto exhibited about 2.9- to about 6.2-fold higher activity for CPC substrate and equivalent to about 2.4-fold higher thermal activity, compared to the wild-type (SEQ ID NO: 1).

Example 6: Comparison of Enzymatic Activity and Thermal Stability of CPC Acylase Mutant According to A11α Mutation With reference to Example 5, CPC acylases were assayed for enzymatic activity and thermal stability according to the mutated residue for A11α.

In brief, site-directed mutagenesis was performed on the wild-type CPC acylase sequence (SEQ ID NO: 1) as a template to afford CPC acylase mutants A11αN, A11αP, A11αQ, A11αI, A11αV, A11αL, and A11αT in which the amino acid residue A11α was substituted with asparagine (N), proline (P), glutamine (Q), isoleucine (I), valine (V), leucine (L), and threonine (T), respectively.

The CPC acylase mutants prepared above and the wild-type CPC acylase were assayed for enzymatic activity for CPC substrate and thermal stability with reference to the methods of Examples 1.3 (enzymatic activity) and 3 (thermal stability, measured using the enzyme solution left at 40° C. for 30 min).

The assay results for the CPC acylase mutants are expressed as relative values (folds) to those of the wild-type CPC acylase in Table 6, below.

TABLE 6

| Mutant Residue | Relative activity for CPC substrate (fold) | Relative activity for thermal stability (fold) |
|---|---|---|
| Wild type | 1.00 | 1.00 |
| A11αT | 0.95 | 0.88 |
| A11αN | 4.70 | 1.07 |
| A11αP | 2.20 | 1.00 |
| A11αQ | 2.90 | 1.00 |
| A11αI | 3.50 | 1.02 |
| A11αV | 3.80 | 1.03 |
| A11αL | 2.70 | 1.05 |

As shown in Table 6, the enzymatic activity for CPC substrate of the CPC acylase mutants A11αN, A11αP, A11αQ, A11αI, A11αV, and A11αL was superior to that of the wild type and about 2.3- to 5-fold higher than that of the CPC acylase mutant A11αT. In addition, the CPC acylase mutants A11αN, A11αP, A11αQ, A11αI, A11αV, and A11αL were equivalent to or higher than the wild type in terms of thermal stability whereas the CPC acylase mutant A11αT was lower in stability than the wild type. Furthermore, the CPC acylase mutants A11αN, A11αP, A11αQ, A11αI, A11αV, and A11αL exhibited about 1.14- to 1.22-fold improved stability, compared to the CPC acylase mutant A11αT.

From the data, it was understood that the mutant CPC acylase in which A11α was substituted with asparagine (N), proline (P), glutamine (Q), isoleucine (I), valine (V), or leucine (L) retained remarkably improved characteristics, compared to the wild type and the mutant in which the same amino acid residue (A11α) was substituted with a different amino acid (e.g., threonine (T)).

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the present disclosure is defined by the appended claims rather than by the description preceding them, and thus all changes and modifications that fall within metes and bounds of the claims or equivalents of such metes and bounds are therefore intended to be embraced by the claims.

[Accession Number]
  Depositary Authority: Korean Collection for Type Culture
  Accession Number: KCTC14821 BP
  Deposition date: Dec. 13, 2021

---

The invention claimed is:

1. A mutant cephalosporin C (CPC) acylase, derived from a CPC acylase comprising an alpha-subunit and a beta-subunit, wherein the mutant CPC acylase comprises a mutation by substitution of isoleucine at position 179 in the beta-subunit of SEQ ID NO: 4 (I179β) with tyrosine (Y) (I179βY), and the mutant CPC acylase has an amino acid sequence having 90% or higher identity with SEQ ID NO:1 and retains a CPC acylase function.

2. The mutant CPC acylase of claim 1, wherein the mutant cephalosporin C (CPC) acylase further comprises a mutation by at least one substitution selected from the group consisting of:
substitution of alanine at position 11 in the alpha-subunit of SEQ ID NO: 3 (A11α) with asparagine (N), proline (P), glutamine (Q), isoleucine (I), valine (V), or leucine (L);
substitution of glycine at position 24 in the alpha-subunit of SEQ ID NO: 3 (G24α) with an amino acid different from the original amino acid residue;
substitution of alanine at position 136 in the beta-subunit of SEQ ID NO: 4 (A136β) with an amino acid different from the original amino acid residue; and
substitution of histidine at position 453 in the beta-subunit of SEQ ID NO: 4 (H453β) with an amino acid different from the original amino acid residue.

3. The mutant CPC acylase of claim 1, wherein the mutant cephalosporin C (CPC) acylase further comprises a mutation by at least one substitution selected from the group consisting of:
substitution of A11α in the alpha-subunit of SEQ ID NO: 3 with asparagine (N), proline (P), glutamine (Q), isoleucine (I), valine (V), or leucine (L);
substitution of G24α in the alpha-subunit of SEQ ID NO: 3 with aspartic acid (D) (G24βD);
substitution of A136β in the beta-subunit of SEQ ID NO: 4 with threonine (T) (A136βT); and
substitution of H453β in the beta-subunit of SEQ ID NO: 4 with threonine (T) (H453βT).

4. The mutant CPC acylase of claim 2, wherein the mutant CPC acylase comprises a mutation by all of the following substitutions:
substitution of alanine at position 11 in the alpha-subunit of SEQ ID NO: 3 (A11α) with asparagine (N);
substitution of glycine at position 24 in the alpha-subunit of SEQ ID NO: 3 (G24α) with an amino acid different from the original amino acid residue;
substitution of alanine at position 136 in the beta-subunit of SEQ ID NO: 4 (A136β) with an amino acid different from the original amino acid residue; and
substitution of isoleucine at position 179 in the beta-subunit of SEQ ID NO: 4 (I179β) with an amino acid different from the original amino acid residue.

5. The mutant CPC acylase of claim 4, wherein the mutant CPC acylase further comprises a mutation by substitution of histidine at position 453 in the beta-subunit of SEQ ID NO: 4 with an amino acid different from the original amino acid residue.

6. The mutant CPC acylase of claim 4, wherein the substitution comprises all of the following substitutions:
substitution of A11α in the alpha-subunit of SEQ ID NO: 3 with asparagine (N) (A11αN);
substitution of G24α in the alpha-subunit of SEQ ID NO: 3 with aspartic acid (D) (G24αD);
substitution of A136β in the beta-subunit of SEQ ID NO: 4 with threonine (T) (A136βT); and
substitution of I1793β in the beta-subunit of SEQ ID NO: 4 with tyrosine (Y) (I179βY).

7. The mutant CPC acylase of claim 6, wherein the mutant CPC acylase further comprises a mutation by substitution of histidine at position 453 in the beta-subunit of SEQ ID NO: 4 (H453β) with an amino acid different from the original amino acid residue.

8. The mutant CPC acylase of claim 7, wherein the substitution of histidine at position 453 is carried out by substituting H453β in the beta-subunit of SEQ ID NO: 4 with threonine (T) (H453βT).

9. The mutant CPC acylase of claim 1, wherein the mutant CPC acylase further comprises a mutation by additional substitution of at least one amino acid selected from the following amino acids in the beta-subunit of SEQ ID NO: 4 with an amino acid different from the corresponding original amino acid:
isoleucine at position 45 (I45β), phenylalanine at position 58 (F58β), tyrosine at position 153 (Y153β), phenylalanine at position 177 (F177β), and valine at position 382 (V382β).

10. The mutant CPC acylase of claim 9, wherein the additional substitution is at least one selected from the group consisting of:
  substitution of 145β with valine (V) (145βV);
  substitution of F58β with valine(V) (F58βV);
  substitution of Y153β with threonine (T) (Y153βT);
  substitution of F177β with leucine (L) (F177βL); and
  substitution of V382β with leucine L) (V382βL),
  in the beta-subunit of SEQ ID NO: 4.

11. The mutant CPC acylase of claim 10, wherein the additional substitution comprises all of the following substitutions:
  substitution of 145β with valine (V) (145βV);
  substitution of F58β with valine(V) (F58βV);
  substitution of Y153β with threonine (T) (Y153βT);
  substitution of F177β with leucine (L) (F177βL); and
  substitution of V382β with leucine L) (V382βL),
  in the beta-subunit of SEQ ID NO: 4.

12. The mutant CPC acylase of claim 10, wherein the mutant CPC acylase is represented by the amino acid sequence of SEQ ID NO: 9 or SEQ ID NO: 12.

13. A nucleic acid molecule, encoding:
  (1) the mutant CPC acylase of claim 1,
  (2) a mutant CPC acylase comprising a mutation by at least one substitution selected from the group consisting of the substitutions of (i) A11α with asparagine (N), proline (P), glutamine (Q), isoleucine (I), valine (V), or leucine (L), (ii) G24α with an amino acid different from the original amino acid residue, (iii) A136β with an amino acid different from the original amino acid residue, and (iv) H453β with an amino acid different from the original amino acid residue, in addition to the mutation in the mutant CPC acylase (1), or
  (3) a mutant CPC acylase comprising a mutation by at least one selected from the group consisting of the substitutions 145βV, F58βV, Y153βT, F177βL, and V382βL in addition to the mutation in the mutant CPC acylase (1) or (2).

14. A recombinant expression vector, carrying the nucleic acid molecule of claim 13.

15. A recombinant cell, comprising the nucleic acid molecule of claim 13.

16. A composition for production of 7-aminocephalosporanic acid (7-ACA) or a salt thereof, the composition comprising at least one selected from the group consisting of:
  (1) the mutant CPC acylase of claim 1;
  (2) a mutant CPC acylase comprising a mutation by at least one substitution selected from the group consisting of the substitutions of (i) A11α with asparagine (N), proline (P), glutamine (Q), isoleucine (I), valine (V), or leucine (L), (ii) G24α with an amino acid different from the original amino acid residue, (iii) A136β with an amino acid different from the original amino acid residue, and (iv) H453β with an amino acid different from the original amino acid residue, in addition to the mutation in the mutant CPC acylase (1),
  (3) a mutant CPC acylase comprising a mutation by at least one substitution selected from the group consisting of 145βV, F58βV, Y153βT, F177βL, and V382βL in addition to the mutation in the mutant CPC acylase (1) or (2);
  (4) a nucleic acid molecule coding for the mutant CPC acylase (1), (2), or (3), or a recombinant expression vector or recombinant cell including the nucleic acid molecule; and
  (5) a recombinant cell comprising the nucleic acid molecule or the recombinant vector, or a culture thereof.

17. A method for producing a compound of Chemical Formula 2 or a salt thereof, the method comprising a step of contacting the composition of claim 16 with a compound of Chemical Formula 1 or a salt thereof:

<Chemical Formula 1>

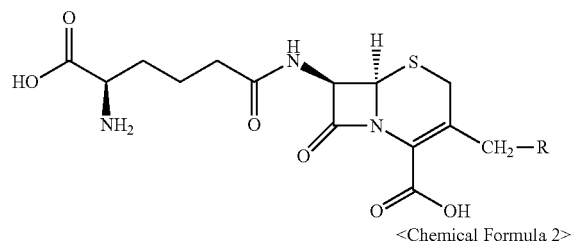

<Chemical Formula 2>

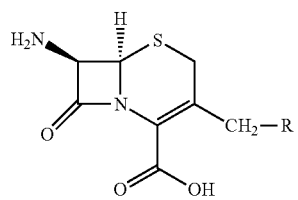

wherein, R is acetoxy(—OCOCH₃), hydroxy (—OH), or hydrogen (—H) group.

18. The mutant CPC acylase of claim 5, wherein the substitution of histidine at position 453 is carried out by substituting H453β in the beta-subunit of SEQ ID NO: 4 with threonine (T) (H453βT).

* * * * *

SEQUENCE LISTING

```
Sequence total quantity: 32
SEQ ID NO: 1            moltype = AA   length = 692
FEATURE                 Location/Qualifiers
REGION                  1..692
                        note = Protein (692 aa) of wild-type Gl-7-ACA acylase from
                        Pseudomonas sp. GK16, comprising alpha- and beta-subunits
                        and a spacer therebetween
source                  1..692
                        mol_type = protein
                        organism = synthetic construct
SEQUENCE: 1
MEPTSTPQAP IAAYKPRSNE ILWDGYGVPH IYGVDAPSAF YGYGWAQARS HGDNILRLYG   60
EARGKGAEYW GPDYEQTTVW LLTNGVPERA QQWYAQQSPD FRANLDAFAA GINAYAQQNP  120
DDISPEVRQV LPVSGADVVA HAHRLMNFLY VASPGRTLGE GDPPDLADQG SNSWAVAPGK  180
TANGNALLLQ NPHLSWTTDY FTYYEAHLVT PDFEIYGATQ IGLPVIRFAF NQRMGITNTV  240
NGMVGATNYR LTLQDGGYLY DGQVRPFERR QASYRLRQAD GTTVDKPLEI RSSVHGPVFE  300
RADGTAVAVR VAGLDRPGML EQYFDMITAD SFDDYEAALA RMQVPTFNIV YADREGTINY  360
SFNGVAPKRA EGDIAFWQGL VPGDSSRYLW TETHPLDDLP RVTNPPGGFV QNSNDPPWTP  420
TWPVTYTPKD FPSYLAPQTP HSLRAQQSVR LMSENDDLTL ERFMALQLSH RAVMADRTLP  480
DLIPAALIDP DPEVQAAARL LAAWDREFTS DSRAALLFEE WARLFAGQNF AGQAGFATPW  540
SLDKPVSTPY GVRDPKAAVD QLRTAIANTK RKYGAIDRPF GDASRMILND VNVPGAAGYG  600
NLGSFRVFTW SDPDENGVRT PVHGETWVAM IEFSTPVRAY GLMSYGNSRQ PGTTHYSDQI  660
ERVSRADFRE LLLRREQVEA AVQERTPFNF KP                                692

SEQ ID NO: 2            moltype = DNA   length = 2079
FEATURE                 Location/Qualifiers
misc_feature            1..2079
                        note = Gene (2079 bp) encoding the protein of SEQ ID NO: 1
source                  1..2079
                        mol_type = other DNA
                        organism = synthetic construct
SEQUENCE: 2
atggaaccga ccagcacccc gcaggctccg atcgctgctt ataaaccgcg tagcaacgaa    60
atcctgtggg atggttatgg tgttccgcat atctatggtg ttgacgctcg gagcgctttt   120
tatggttatg gctgggctca ggctcgtagc catggtgata acatcctgcg tctgtatggt   180
gaagctcgtg gtaaaggcgc tgaatattgg ggtccggatt acgaacagac gaccgtttgg   240
ctgctgacca acggtgttcc ggaacgtgct cagcagtggt atgctcagca gagcccggat   300
tttcgtgcta acctggatgc ttttgctgct ggtatcaacg cttatgctca gcagaacccg   360
gatgatatca gcccggaagt tcgtcaggtt ctgccggtta gcggtgctga tgttgttgct   420
catgctcatc gtctgatgaa ctttctgtat gttgctagcc cgggtcgtac cctgggtgaa   480
ggtgatccgc cggatctggc tgatcagggt agcaacagct gggctgttgc tccgggtaaa   540
accgctaacg gtaacgctct gctgctgcag aaccctcatc tgagctggac caccgattab   600
tttacctatt atgaagctca tctggttacc ccggattttg aaatctatgg tgctacccag   660
atcggtctgc cggttatccg ttttgctttt aaccagcgta tgggtatcac caacaccgtt   720
aacggtatgg ttggtgctac caactatcgt ctgaccctgc aggatggtgg ttatctgtat   780
gatggtcagg ttcgtccgtt tgaacgtcgt caggctgatc atcgtctggc tcaggctgat   840
ggtaccaccg ttgataaacc gctggaaatc cgttccagcg ttcatggtcc ggttttgaa    900
cgtgctgatg gtaccgctgt tgctgttcgt gttgctggtc tggatcgtcc gggtatgctg   960
gaacagtatt ttgatatgat caccgctgat agctttgatg attatgaagc tgctctggct  1020
cgtatgcagg ttccgacctt taacatcgtt tatgctgatc gtgaaggtac catcaactat  1080
agctttaacg gtgttgctcc gaaacgtgct gaaggtgaca tcgcttttg gcagggtctg  1140
gttccgggtg atagcagccg ttatctgtgg accgaaaccc atccgctgga tgatctgccg  1200
cgtgttacca acccgccggg tggttttgtt cagaacagca acgatccgcc gtggacccg   1260
acctggccgg ttacctatac cccgaaagat tttccgagct atctggctcc gcagacccg   1320
catagcctgc gtgctcagca gagcgttcgt ctgatgagcg aaaacgatga tctgaccctg  1380
gaacgtttta tggctctgca gctgagccat cgtgctgtta tggctgatcg tacctgccg   1440
gatctgatcc cggctgctct gatcgatccg gatccggaag ttcaggctgc tgctcgtctg  1500
ctggctgcgt gggatcgtga atttaccagc gatagccgtg ctgctctgct gtttgaagaa  1560
tgggctcgtc tgtttgctgg tcagaacttt gctggtcagg ctggctttgc tacccctgtg  1620
agcctggata aaccggttag cacccctat ggtgttccgt atccgaaagc tgctgttgat  1680
```

```
cagctgcgta ccgctatcgc taacaccaaa cgtaaatatg gtgctatcga tcgtccgttt       1740
ggtgatgcta gccgtatgat cctgaacgat gttaacgttc cgggtgctgc tggttatggt       1800
aacctgggta gctttcgtgt ttttacctgg agcgatccgg atgaaaacgg tgtgcgtacc       1860
ccggttcatg gtgaaacctg ggttgctatg atcgaattta gcaccccggt tcgtgcttat       1920
ggtctgatga gctatggtaa cagccgtcag ccgggtacca cccattatag cgatcagatc       1980
gaacgtgtta gccgtgctga ttttcgtgaa ctgctgctgc gtcgtgaaca ggttgaagct       2040
gctgttcagg aacgtacccc gtttaacttt aaaccgtga                              2079
```

```
SEQ ID NO: 3              moltype = AA   length = 158
FEATURE                   Location/Qualifiers
REGION                    1..158
                          note = Alpha-subunit (158 aa) of wild-type G1-7-ACA acylase
                           protein from Pseudomonas sp. GK16
source                    1..158
                          mol_type = protein
                          organism = synthetic construct
SEQUENCE: 3
EPTSTPQAPI AAYKPRSNEI LWDGYGVPHI YGVDAPSAFY GYGWAQARSH GDNILRLYGE        60
ARGKGAEYWG PDYEQTTVWL LTNGVPERAQ QWYAQQSPDF RANLDAFAAG INAYAQQNPD       120
DISPEVRQVL PVSGADVVAH AHRLMNFLYV ASPGRTLG                               158

SEQ ID NO: 4              moltype = AA   length = 522
FEATURE                   Location/Qualifiers
REGION                    1..522
                          note = Beta-subunit (522 aa) of wild-type G1-7-ACA acylase
                           protein
source                    1..522
                          mol_type = protein
                          organism = synthetic construct
SEQUENCE: 4
SNSWAVAPGK TANGNALLLQ NPHLSWTTDY FTYYEAHLVT PDFEIYGATQ IGLPVIRFAF        60
NQRMGITNTV NGMVGATNYR LTLQDGGYLY DGQVRPFERR QASYRLRQAD GTTVDKPLEI       120
RSSVHGPVFE RADGTAVAVR VAGLDRPGML EQYFDMITAD SFDDYEAALA RMQVPTFNIV       180
YADREGTINY SFNGVAPKRA EGDIAFWQGL VPGDSSRYLW TETHPLDDLP RVTNPPGGFV       240
QNSNDPPWTP TWPVTYTPKD FPSYLAPQTP HSLRAQQSVR LMSENDDLTL ERFMALQLSH       300
RAVMADRTLP DLIPAALIDP DPEVQAAARL LAAWDREFTS DSRAALLFEE WARLFAGQNF       360
AGQAGFATPW SLDKPVSTPY GVRDPKAAVD QLRTAIANTK RKYGAIDRPF GDASRMILND       420
VNVPGAAGYG NLGSFRVFTW SDPDENGVRT PVHGETWVAM IEFSTPVRAY GLMSYGNSRQ       480
PGTTHYSDQI ERVSRADFRE LLLRREQVEA AVQERTPFNF KP                          522

SEQ ID NO: 5              moltype = AA   length = 11
FEATURE                   Location/Qualifiers
REGION                    1..11
                          note = Spacer (11 aa)
source                    1..11
                          mol_type = protein
                          organism = synthetic construct
SEQUENCE: 5
EGDPPDLADQ G                                                             11

SEQ ID NO: 6              moltype = AA   length = 692
FEATURE                   Location/Qualifiers
REGION                    1..692
                          note = PM2 mutant (692 aa) comprising wild-type
                           alpha-subunit of G1-7-ACA asylase from GK16, and mutant
                           beta-subunit, and a spacer therebetween
source                    1..692
                          mol_type = protein
                          organism = synthetic construct
SEQUENCE: 6
MEPTSTPQAP IAAYKPRSNE ILWDGYGVPH IYGVDAPSAF YGYGWAQARS HGDNILRLYG        60
EARGKGAEYW GPDYEQTTVW LLTNGVPERA QQWYAQQSPD FRANLDAFAA GINAYAQQNP       120
DDISPEVRQV LPVSGADVVA HAHRLMNFLY VASPGRTLGE GDPPDLADQG SNSWAVAPGK       180
TANGNALLLQ NPHLSWTTDY FTYYEAHLVT PDFEVYGATQ IGLPVIRVAF NQRMGITNTV       240
NGMVGATNYR LTLQDGGYLY DGQVRPFERR QASYRLRQAD GTTVDKPLEI RSSVHGPVFE       300
RADGTAVAVR VAGLDRPGML EQTFDMITAD SFDDYEAALA RMQVPTLNIV YADREGTINY       360
SFNGVAPKRA EGDIAFWQGL VPGDSSRYLW TETHPLDDLP RVTNPPGGFV QNSNDPPWTP       420
TWPVTYTPKD FPSYLAPQTP HSLRAQQSVR LMSENDDLTL ERFMALQLSH RAVMADRTLP       480
DLIPAALIDP DPEVQAAARL LAAWDREFTS DSRAALLFEE WARLFAGQNF AGQAGFATPW       540
SLDKPVSTPY GLRDPKAAVD QLRTAIANTK RKYGAIDRPF GDASRMILND VNVPGAAGYG       600
NLGSFRVFTW SDPDENGVRT PVHGETWVAM IEFSTPVRAY GLMSYGNSRQ PGTTHYSDQI       660
ERVSRADFRE LLLRREQVEA AVQERTPFNF KP                                    692

SEQ ID NO: 7              moltype = DNA   length = 2079
FEATURE                   Location/Qualifiers
misc_feature              1..2079
                          note = Gene (2079 bp) encoding PM2 mutant
source                    1..2079
                          mol_type = other DNA
```

```
                        organism = synthetic construct
SEQUENCE: 7
atggaaccga ccagcacccc gcaggctccg atcgctgctt ataaaccgcg tagcaacgaa   60
atcctgtggg atggttatgg tgttccgcat atctatggtg ttgacgctcc gagcgctttt  120
tatggttatg gctgggctca ggctcgtagc catggtgata acatcctgcg tctgtatggt  180
gaagctcgtg gtaaaggcgc tgaatattgg ggtccggatt acgaacagac gaccgtttgg  240
ctgctgacca acggtgttcc ggaacgtgct cagcagtggt atgctcagca gagcccggat  300
tttcgtgcta acctggatgc ttttgctgct ggtatcaacg cttatgctca gcagaacccg  360
gatgatatca gcccggaagt tcgtcaggtt ctgccggtta gcggtgctga tgttgttgct  420
catgctcatc gtctgatgaa ctttctgtat gttgctagcc cggtcgtac cctgggtgaa   480
ggtgatccgc cggatctggc tgatcagggt agcaacagct gggctgttgc tccgggtaaa  540
accgctaacg gtaacgctct gctgctgcag aaccctcatc tgagctggac caccgattat  600
tttacctatt atgaagctca tctggttacc ccggattttg aagtgtatgg tgctacccag  660
atcggtctgc cggttatccg tgttgctttt aaccagcgta tgggtatcac caacaccgtt  720
aacggtatgg ttggtgctac caactatcgt ctgaccctgc aggatggtgg ttatctgtat  780
gatggtcagg ttcgtccgtt tgaacgtcgt caggctagtc atcgtctgcg tcaggctgat  840
ggtaccaccg ttgataaacc gctggaaatc cgttccagcg ttcatggtcc ggtttttgaa  900
cgtgctgatg gtaccgctgt tgctgttcgt gttgctggtc tggatcgtcc gggtatgctg  960
gaacagactt tgatatgat caccgctgat agctttgatg attatgaagc tgctctggct  1020
cgtatgcagg ttccgacctt gaacatcgtt tatgctgatc gtgaaggtac catcaactat  1080
agctttaacg gtgttgctcc gaaacgtgct gaaggtgaca tcgcttttgg gcagggtctg  1140
gttccgggtg atagcagccg ttatctgtgg accgaaaccc atccgctgga tgatctgccg  1200
cgtgttacca acccgccggg tggttttgtt cagaacagca cgatccgcc gtggaccccg  1260
acctggccgg ttacctatac cccgaaagat tttccgagct atctggctcc gcagacccg   1320
catagcctgc gtgctcagca gagcgttcgt ctgatgagcg aaaacgatga tctgaccctg  1380
gaacgttta tggctctgca gctgagccat cgtgctgtta tacccctgcg             1440
gatctgatcc cggctgctct gatcgatccg gatccggaag ttcaggctgc tgctcgtctg  1500
ctggctgcgt gggatcgtga atttaccagc gatagccgtg ctgctctgct gtttgaagaa  1560
tgggctcgtc tgtttgctgg tcagaacttt gctggtcagg ctggctttgc taccccgtgg  1620
agcctggata aacggttag caccccgtat ggtctgcgtg atccgaaagc tgctgttgat  1680
cagctgcgta ccgctatcgc taacaccaaa cgtaaatatg gtgctatcga tcgtccgttt  1740
ggtgatgcta gccgtatgat cctgaacgat gttaacgttc cgggtgctgc tggttatggt  1800
aacctgggta gctttcgtgt ttttacctgg agcgatccgg atgaaaacgg tgtgcgtacc  1860
ccggttcatg gtgaaacctg gttgctatg atcgaattta gcaccccggt tcgtgcttat   1920
ggtctgatga gctatggtaa cagccgtcag ccgggtacca ccattatgac cgatcagatc  1980
gaacgtgtta gccgtgctga ttttcgtgaa ctgctgctgc gtcgtgaaca ggttgaagct  2040
gctgttcagg aacgtacccc gtttaacttt aaaccgtga                         2079

SEQ ID NO: 8            moltype = AA  length = 522
FEATURE                 Location/Qualifiers
REGION                  1..522
                        note = Beta-subunit of mutant PM2 protein
source                  1..522
                        mol_type = protein
                        organism = synthetic construct
SEQUENCE: 8
SNSWAVAPGK TANGNALLLQ NPHLSWTTDY FTYYEAHLVT PDFEVYGATQ IGLPVIRVAF   60
NQRMGITNTV NGMVGATNYR LTLQDGGYLY DGQVRPFERR QASYRLRQAD GTTVDKPLEI  120
RSSVHGPVFE RADGTAVAVR VAGLDRPGML EQTFDMITAD SFDDYEAALA RMQVPTLNIV  180
YADREGTINY SFNGVAPKRA EGDIAFWQGL VPGDSSRYLW TETHPLDDLP RVTNPPGGFV  240
QNSNDPPWTP TWPVTYTPKD FPSYLAPQTP HSLRAQQSVR LMSENDDLTL ERFMALQLSH  300
RAVMADRTLP DLIPAALIDP DPEVQAAARL LAAWDREFTS DSRAALLFEE WARLFAGQNF  360
AGQAGFATPW SLDKPVSTPY GLRDPKAAVD QLRTAIANTK RKYGAIDRPF GDASRMILND  420
VNVPGAAGYG NLGSFRVFTW SDPDENGVRT PVHGETWVAM IEFSTPVRAY GLMSYGNSRQ  480
PGTTHYSDQI ERVSRADFRE LLLRREQVEA AVQERTPFNF KP                     522

SEQ ID NO: 9            moltype = AA  length = 692
FEATURE                 Location/Qualifiers
REGION                  1..692
                        note = mutant CSH17 protein
source                  1..692
                        mol_type = protein
                        organism = synthetic construct
SEQUENCE: 9
MEPTSTPQAP INAYKPRSNE ILWDDYGVPH IYGVDAPSAF YGYGWAQARS HGDNILRLYG   60
EARGKGAEYW GPDYEQTTVW LLTNGVPERA QQWYAQQSPD FRANLDAFAA GINAYAQQNP  120
DDISPEVRQV LPVSGADVVA HAHRLMNFLY VASPGRTLGE GDPPDLADQG SNSWAVAPGK  180
TANGNALLLQ NPHLSWTTDY FTYYEAHLVT PDFEVYGATQ IGLPVIRVAF NQRMGITNTV  240
NGMVGATNYR LTLQDGGYLY DGQVRPFERR QASYRLRQAD GTTVDKPLEI RSSVHGPVFE  300
RADGTTVAVR VAGLDRPGML EQTFDMITAD SFDDYEAALA RMQVPTLNYV YADREGTINY  360
SFNGVAPKRA EGDIAFWQGL VPGDSSRYLW TETHPLDDLP RVTNPPGGFV QNSNDPPWTP  420
TWPVTYTPKD FPSYLAPQTP HSLRAQQSVR LMSENDDLTL ERFMALQLSH RAVMADRTLP  480
DLIPAALIDP DPEVQAAARL LAAWDREFTS DSRAALLFEE WARLFAGQNF AGQAGFATPW  540
SLDKPVSTPY GLRDPKAAVD QLRTAIANTK RKYGAIDRPF GDASRMILND VNVPGAAGYG  600
NLGSFRVFTW SDPDENGVRT PVHGETWVAM IEFSTPVRAY GLMSYGNSRQ PGTTHYSDQI  660
ERVSRADFRE LLLRREQVEA AVQERTPFNF KP                                692

SEQ ID NO: 10           moltype = AA  length = 158
FEATURE                 Location/Qualifiers
```

```
REGION                         1..158
                               note = Alpha-subunit of mutant CSH17 protein
source                         1..158
                               mol_type = protein
                               organism = synthetic construct
SEQUENCE: 10
EPTSTPQAPI NAYKPRSNEI LWDDYGVPHI YGVDAPSAFY GYGWAQARSH GDNILRLYGE    60
ARGKGAEYWG PDYEQTTVWL LTNGVPERAQ QWYAQQSPDF RANLDAFAAG INAYAQQNPD   120
DISPEVRQVL PVSGADVVAH AHRLMNFLYV ASPGRTLG                           158

SEQ ID NO: 11                  moltype = AA   length = 522
FEATURE                        Location/Qualifiers
REGION                         1..522
                               note = Beta-subunit of mutant CSH17 protein
source                         1..522
                               mol_type = protein
                               organism = synthetic construct
SEQUENCE: 11
SNSWAVAPGK TANGNALLLQ NPHLSWTTDY FTYYEAHLVT PDFEVYGATQ IGLPVIRVAF    60
NQRMGITNTV NGMVGATNYR LTLQDGGYLY DGQVRPFERR QASYRLRQAD GTTVDKPLEI   120
RSSVHGPVFE RADGTTVAVR VAGLDRPGML EQTFDMITAD SFDDYEAALA RMQVPTLNYV   180
YADREGTINY SFNGVAPKRA EGDIAFWQGL VPGDSSRYLW TETHPLDDLP RVTNPPGGFV   240
QNSNDPPWTP TWPVTYTPKD FPSYLAPQTP HSLRAQQSVR LMSENDDLTL ERFMALQLSH   300
RAVMADRTLP DLIPAALIDP DPEVQAAARL LAAWDREFTS DSRAALLFEE WARLFAGQNF   360
AGQAGFATPW SLDKPVSTPY GLRDPKAAVD QLRTAIANTK RKYGAIDRPF GDASRMILND   420
VNVPGAAGYG NLGSFRVFTW SDPDENGVRT PVHGETWVAM IEFSTPVRAY GLMSYGNSRQ   480
PGTTHYSDQI ERVSRADFRE LLLRREQVEA AVQERTPFNF KP                     522

SEQ ID NO: 12                  moltype = AA   length = 692
FEATURE                        Location/Qualifiers
REGION                         1..692
                               note = mutant TEP11 protein
source                         1..692
                               mol_type = protein
                               organism = synthetic construct
SEQUENCE: 12
MEPTSTPQAP INAYKPRSNE ILWDDYGVPH IYGVDAPSAF YGYGWAQARS HGDNILRLYG    60
EARGKGAEYW GPDYEQTTVW LLTNGVPERA QQWYAQQSPD FRANLDAFAA GINAYAQQNP   120
DDISPEVRQV LPVSGADVVA HAHRLMNFLY VASPGRTLGE GDPPDLADQG SNSWAVAPGK   180
TANGNALLLQ NPHLSWTTDY FTYYEAHLVT PDFEVYGATQ IGLPVIRVAF NQRMGITNTV   240
NGMVGATNYR LTLQDGGYLY DGQVRPFERR QASYRLRQAD GTTVDKPLEI RSSVHGPVFE   300
RADGTTVAVR VAGLDRPGML EQTFDMITAD SFDDYEAALA RMQVPTLNYV YADREGTINY   360
SFNGVAPKRA EGDIAFWQGL VPGDSSRYLW TETHPLDDLP RVTNPPGGFV QNSNDPPWTP   420
TWPVTYTPKD FPSYLAPQTP HSLRAQQSVR LMSENDDLTL ERFMALQLSH RAVMADRTLP   480
DLIPAALIDP DPEVQAAARL LAAWDREFTS DSRAALLFEE WARLFAGQNF AGQAGFATPW   540
SLDKPVSTPY GLRDPKAAVD QLRTAIANTK RKYGAIDRPF GDASRMILND VNVPGAAGYG   600
NLGSFRVFTW SDPDENGVRT PVTGETWVAM IEFSTPVRAY GLMSYGNSRQ PGTTHYSDQI   660
ERVSRADFRE LLLRREQVEA AVQERTPFNF KP                                 692

SEQ ID NO: 13                  moltype = AA   length = 158
FEATURE                        Location/Qualifiers
REGION                         1..158
                               note = Alpha-subunit of mutant TEP11 protein
source                         1..158
                               mol_type = protein
                               organism = synthetic construct
SEQUENCE: 13
EPTSTPQAPI NAYKPRSNEI LWDDYGVPHI YGVDAPSAFY GYGWAQARSH GDNILRLYGE    60
ARGKGAEYWG PDYEQTTVWL LTNGVPERAQ QWYAQQSPDF RANLDAFAAG INAYAQQNPD   120
DISPEVRQVL PVSGADVVAH AHRLMNFLYV ASPGRTLG                           158

SEQ ID NO: 14                  moltype = AA   length = 522
FEATURE                        Location/Qualifiers
REGION                         1..522
                               note = Beta-subunit of mutant TEP11
source                         1..522
                               mol_type = protein
                               organism = synthetic construct
SEQUENCE: 14
SNSWAVAPGK TANGNALLLQ NPHLSWTTDY FTYYEAHLVT PDFEVYGATQ IGLPVIRVAF    60
NQRMGITNTV NGMVGATNYR LTLQDGGYLY DGQVRPFERR QASYRLRQAD GTTVDKPLEI   120
RSSVHGPVFE RADGTTVAVR VAGLDRPGML EQTFDMITAD SFDDYEAALA RMQVPTLNYV   180
YADREGTINY SFNGVAPKRA EGDIAFWQGL VPGDSSRYLW TETHPLDDLP RVTNPPGGFV   240
QNSNDPPWTP TWPVTYTPKD FPSYLAPQTP HSLRAQQSVR LMSENDDLTL ERFMALQLSH   300
RAVMADRTLP DLIPAALIDP DPEVQAAARL LAAWDREFTS DSRAALLFEE WARLFAGQNF   360
AGQAGFATPW SLDKPVSTPY GLRDPKAAVD QLRTAIANTK RKYGAIDRPF GDASRMILND   420
VNVPGAAGYG NLGSFRVFTW SDPDENGVRT PVTGETWVAM IEFSTPVRAY GLMSYGNSRQ   480
PGTTHYSDQI ERVSRADFRE LLLRREQVEA AVQERTPFNF KP                     522
```

```
SEQ ID NO: 15           moltype = DNA  length = 20
FEATURE                 Location/Qualifiers
misc_feature            1..20
                        note = T3 primer
source                  1..20
                        mol_type = other DNA
                        organism = synthetic construct
SEQUENCE: 15
aattaaccct cactaaaggg                                                   20

SEQ ID NO: 16           moltype = DNA  length = 20
FEATURE                 Location/Qualifiers
misc_feature            1..20
                        note = T7 primer
source                  1..20
                        mol_type = other DNA
                        organism = synthetic construct
SEQUENCE: 16
taatacgact cactataggg                                                   20

SEQ ID NO: 17           moltype = DNA  length = 20
FEATURE                 Location/Qualifiers
misc_feature            1..20
                        note = M13-F primer
source                  1..20
                        mol_type = other DNA
                        organism = synthetic construct
SEQUENCE: 17
ttgtaaaacg acggccagtg                                                   20

SEQ ID NO: 18           moltype = DNA  length = 19
FEATURE                 Location/Qualifiers
misc_feature            1..19
                        note = M13-R primer
source                  1..19
                        mol_type = other DNA
                        organism = synthetic construct
SEQUENCE: 18
ggaaacagct atgaccatg                                                    19

SEQ ID NO: 19           moltype = DNA  length = 30
FEATURE                 Location/Qualifiers
misc_feature            1..30
                        note = SH24a-F primer (non-opti)
source                  1..30
                        mol_type = other DNA
                        organism = synthetic construct
SEQUENCE: 19
gaaatcctgt gggatgryta tggtgttccg                                        30

SEQ ID NO: 20           moltype = DNA  length = 30
FEATURE                 Location/Qualifiers
misc_feature            1..30
                        note = SH24a-R primer
source                  1..30
                        mol_type = other DNA
                        organism = synthetic construct
SEQUENCE: 20
cggaacacca tarycatccc acaggatttc                                        30

SEQ ID NO: 21           moltype = DNA  length = 33
FEATURE                 Location/Qualifiers
misc_feature            1..33
                        note = SH179b-F primer
source                  1..33
                        mol_type = other DNA
                        organism = synthetic construct
SEQUENCE: 21
gttccgaccc ttaacwwygt ttatgctgat cgt                                    33

SEQ ID NO: 22           moltype = DNA  length = 33
FEATURE                 Location/Qualifiers
misc_feature            1..33
                        note = SH179b-R primer
source                  1..33
                        mol_type = other DNA
                        organism = synthetic construct
SEQUENCE: 22
acgatcagca taaacrwwgt taagggtcgg aac                                    33
```

```
SEQ ID NO: 23              moltype = DNA   length = 34
FEATURE                    Location/Qualifiers
misc_feature               1..34
                           note = SM7_F priemr
source                     1..34
                           mol_type = other DNA
                           organism = synthetic construct
SEQUENCE: 23
gttccgacct taactatgt ttatgctgat cgtg                                    34

SEQ ID NO: 24              moltype = DNA   length = 34
FEATURE                    Location/Qualifiers
misc_feature               1..34
                           note = SM7_R priemr
source                     1..34
                           mol_type = other DNA
                           organism = synthetic construct
SEQUENCE: 24
cacgatcagc ataaacatag ttaaaggtcg gaac                                   34

SEQ ID NO: 25              moltype = DNA   length = 36
FEATURE                    Location/Qualifiers
misc_feature               1..36
                           note = SM10_F priemr
source                     1..36
                           mol_type = other DNA
                           organism = synthetic construct
SEQUENCE: 25
gaaatcctgt gggatgacta tggtgttccg catatc                                 36

SEQ ID NO: 26              moltype = DNA   length = 36
FEATURE                    Location/Qualifiers
misc_feature               1..36
                           note = SM10_R priemr
source                     1..36
                           mol_type = other DNA
                           organism = synthetic construct
SEQUENCE: 26
gatatgcgga acaccatagt catcccacag gatttc                                 36

SEQ ID NO: 27              moltype = DNA   length = 34
FEATURE                    Location/Qualifiers
misc_feature               1..34
                           note = SM25_F priemr
source                     1..34
                           mol_type = other DNA
                           organism = synthetic construct
SEQUENCE: 27
cgtgctgatg gtaccaccgt tgctgttcgt gttg                                   34

SEQ ID NO: 28              moltype = DNA   length = 34
FEATURE                    Location/Qualifiers
misc_feature               1..34
                           note = SM25_R priemr
source                     1..34
                           mol_type = other DNA
                           organism = synthetic construct
SEQUENCE: 28
caacacgaac agcaacggtg gtaccatcag cacg                                   34

SEQ ID NO: 29              moltype = DNA   length = 36
FEATURE                    Location/Qualifiers
misc_feature               1..36
                           note = SM43_F priemr
source                     1..36
                           mol_type = other DNA
                           organism = synthetic construct
SEQUENCE: 29
ccgcaggctc cgatcaatgc ttataaaccg cgtagc                                 36

SEQ ID NO: 30              moltype = DNA   length = 36
FEATURE                    Location/Qualifiers
misc_feature               1..36
                           note = SM43_R priemr
source                     1..36
                           mol_type = other DNA
                           organism = synthetic construct
SEQUENCE: 30
```

```
                                                       -continued gctacgcggt ttataagcat tgatcggagc ctgcgg                                  36

SEQ ID NO: 31           moltype = DNA  length = 35
FEATURE                 Location/Qualifiers
misc_feature            1..35
                        note = SM52_F priemr
source                  1..35
                        mol_type = other DNA
                        organism = synthetic construct
SEQUENCE: 31
gtgcgtaccc cggttacggg tgaaacctgg gttgc                                   35

SEQ ID NO: 32           moltype = DNA  length = 35
FEATURE                 Location/Qualifiers
misc_feature            1..35
                        note = SM52_R priemr
source                  1..35
                        mol_type = other DNA
                        organism = synthetic construct
SEQUENCE: 32
gcaacccagg tttcacccgt aaccggggta cgcac                                   35
```